(12) United States Patent
Stone

(10) Patent No.: US 6,231,608 B1
(45) Date of Patent: *May 15, 2001

(54) ALDEHYDE AND GLYCOSIDASE-TREATED SOFT AND BONE TISSUE XENOGRAFTS

(75) Inventor: Kevin R. Stone, Mill Valley, CA (US)

(73) Assignee: Crosscart, Inc., Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/248,476

(22) Filed: Feb. 11, 1999

Related U.S. Application Data

(63) Continuation-in-part of application No. 09/036,171, filed on Mar. 6, 1998, now Pat. No. 5,984,858, which is a continuation-in-part of application No. 08/483,256, filed on Jun. 7, 1995, now Pat. No. 5,865,849.

(51) Int. Cl.$^7$ ........................................ A61F 2/28
(52) U.S. Cl. ........................................ 623/16.11
(58) Field of Search ........................ 623/11.11, 13.11, 623/13.17, 16.11, 23.6, 23.61, 23.64, 23.72, 23.75, 23.76; 424/423, 422, 548, 549; 435/1.1, 1.3; 600/36

(56) References Cited

U.S. PATENT DOCUMENTS

| 4,034,418 | 7/1977 | Jackson et al. | 3/1.911 |
| 4,344,193 | 8/1982 | Kenny | 3/1.911 |

(List continued on next page.)

FOREIGN PATENT DOCUMENTS

| WO 84/03036 | 8/1984 | (WO) . |
| WO 95/26740 | 10/1995 | (WO) . |
| WO 95/28412 | 10/1995 | (WO) . |
| WO 95/33828 | 12/1995 | (WO) . |

OTHER PUBLICATIONS

Rodrigo et al., "Osteocartilaginous Allografts as Compared with Autografts in the Treatment of Knee Joint Osteocartilaginous Defects in Dogs", Clinical Orthopedics and Related Research, 134, pp. 342–349 (1978).

Sengupta et al., "The Fate of Transplants of Articular Cartilage in the Rabbit", The Journal of Bone and Joint Surgery, 56B, pp. 167–177 (1974).

(List continued on next page.)

*Primary Examiner*—David J. Isabella
(74) *Attorney, Agent, or Firm*—McDermott, Will & Emery

(57) ABSTRACT

The invention provides articles of manufacture comprising substantially non-immunogenic soft and bone tissue xenografts for implantation into humans. The invention further provides methods for preparing soft and bone tissue xenografts by removing at least a portion of a soft or bone tissue from a non-human animal to provide a xenograft; washing the xenograft in saline and alcohol; subjecting the xenograft to cellular disruption treatment; exposing the xenograft to an aldehyde in an amount ranging from about 0.01% to about 0.10%; and digesting the xenograft with a glycosidase and optionally following with a capping treatment. The invention also provides an article of manufacture produced by the above-identified method of the invention. The invention further provides a soft or bone tissue xenograft for implantation into a human including a portion of a soft or bone tissue from a non-human animal, wherein the portion has extracellular components and substantially only dead cells. The extracellular components have substantially no surface carbohydrate moieties which are susceptible to glycosidase digestion. The extracellular components also have an aldehyde in an amount ranging from about 0.01% to about 0.10% crosslinking the proteins of the extracellular components. Each of the xenografts of the invention are substantially non-immunogenic and have substantially the same mechanical properties as a corresponding native soft or bone tissue.

59 Claims, 7 Drawing Sheets

U.S. PATENT DOCUMENTS

| | | | |
|---|---|---|---|
| 4,400,833 | 8/1983 | Kurland | 3/1 |
| 4,502,161 | 3/1985 | Wall | 3/1.91 |
| 4,597,266 | 7/1986 | Entrekin | 62/46 |
| 4,609,627 | 9/1986 | Goldstein | 435/269 |
| 4,627,853 | 12/1986 | Campbell et al. | 623/16 |
| 4,642,120 | 2/1987 | Nevo et al. | 623/16 |
| 4,678,470 | 7/1987 | Nashef et al. | 623/16 |
| 4,755,593 | 7/1988 | Lauren | 530/356 |
| 4,776,853 | 10/1988 | Klement et al. | 8/94.11 |
| 4,789,663 | 12/1988 | Wallace et al. | 514/21 |
| 4,801,299 | 1/1989 | Brendel et al. | |
| 4,846,835 | 7/1989 | Grande | 623/11 |
| 4,880,429 | 11/1989 | Stone | 623/18 |
| 4,932,973 | 6/1990 | Gendler | 623/16 |
| 5,007,934 | 4/1991 | Stone | 623/20 |
| 5,067,962 | 11/1991 | Campbell et al. | 623/13 |
| 5,071,741 | 12/1991 | Brockbank | 435/1 |
| 5,078,744 | 1/1992 | Chvapil | 623/13 |
| 5,092,894 | 3/1992 | Kenny | 623/18 |
| 5,116,374 | 5/1992 | Stone | 623/16 |
| 5,131,850 | 7/1992 | Brockbank | 435/1 |
| 5,158,574 | 10/1992 | Stone | 623/66 |
| 5,160,313 | 11/1992 | Carpenter et al. | 600/36 |
| 5,171,273 | 12/1992 | Silver et al. | 623/13 |
| 5,171,322 | 12/1992 | Kenny | 623/18 |
| 5,171,660 | 12/1992 | Carpenter et al. | 435/1 |
| 5,192,312 | 3/1993 | Orton | 623/2 |
| 5,216,126 | 6/1993 | Cox et al. | 530/350 |
| 5,306,304 | 4/1994 | Gendler | 623/16 |
| 5,306,311 | 4/1994 | Stone et al. | 623/18 |
| 5,333,626 | 8/1994 | Morse et al. | 128/898 |
| 5,358,525 | 10/1994 | Fox et al. | 623/18 |
| 5,507,810 | 4/1996 | Prewett et al. | 623/11 |
| 5,516,532 | 5/1996 | Atala et al. | 424/548 |
| 5,613,982 | 3/1997 | Goldstein | 623/11 |
| 5,782,915 * | 7/1998 | Stone | 623/11 |
| 5,865,849 * | 2/1999 | Stone | 623/18 |
| 5,913,900 * | 6/1999 | Stone | 623/20 |
| 5,922,027 * | 7/1999 | Stone | 623/11 |
| 5,944,755 * | 8/1999 | Stone | 623/16 |

OTHER PUBLICATIONS

Webber et al., "Cell Culture of Rabbit Meniscal Fibrochondrocytes: Proliferative and Synthetic Response to Growth Factors and Ascorbate", Journal of Orthopedic Research, 3, pp. 36–42 (1985).

Rubak et al., "Condrogenesis in Repair of Articular Cartilage Defects by Free Periosteal Grafts in Rabbits", Acta Orthop Scand, 53, pp. 181–186 (1982).

Engkvist, Ove, "Reconstruction of Patellar Articular Cartilage with Free Autologous Perichondrial Grafts", Scand. J. Plast. Reconstr. Surg., 13, pp. 361–369 (1982).

Collins et al., "Characterization of Porcine Endothelial Cell Determinants Recognized by Human Natural Antibodies", Xenotransplantation, 1, pp. 36–46 (1994).

Satake et al., "Limited Specificity of Xenoantibodies in Diabetic Patients Transplanted With Fetal Porcine Islet Cell Clusters, Main Antibody Reactivity Against α–linked Galactose–Containing Epitopes, Xenotransplanation", 1, pp. 89–101 (1994).

LaVecchio et al., "Enzymatic Removal of Alpha–Galactosyl Epitopes From Porcine Endothelial Cells Diminishes The Cytotoxic Effect of Natural Antibodies", Transplantation, 60, pp. 841–847 (1995).

Stone et al., "Surgical Technique of Meniscal Replacment", Arthroscopy: The Journal of Arthroscopic and Related Surgery, 9, pp. 234–237 (1993).

Cotterell et al., "The Humoral Immune Response in Humans Following Cross–Perfusion of Porcine Organs", Transplantation, 60, pp. 861–868 (1995).

Fadali et al., "The Use of Autogenous Peritoneum for Heart Valve Replacement", The Journal of Thoracic and Cardiovascular Surgery, 60:2, pp. 188–195 (1970).

Galili, "Interaction of the Natural Anti–Gal Antibody with α–Galactosyl Epitopes: a Major Obstacle for Xenotransplantation in Humans", Immunology Today, 14, pp. 480–482 (1993).

Elves et al., "An Investigation Into The Immunogenicity Of Various Components of Osteorticular Grafts", The British Journal of Experimental Pathology, 55, pp. 344–351 (1974).

Derby et al., "The Histochemical Specificity of Streptomyces, Hyaluronidase and Chondroitinase ABC", Histochemical Journal, 10, pp. 529–547 (1978).

Homandberg et al., "High Concentrations of Fibronectin Fragments Cause Short–Term Catabolic Effects in Cartilage Tissue While Lower Concentrations Cause Continuous Anabolic Effects", Archives of Biochemistry and Biophysics, 311:2, pp. 213–218 (1994).

Homandberg et al., "Agents that Block Fibronectin Fragment–Mediated Cartilage Damage also Promote Repair", Inflamm. Res., 46, pp. 467–471 (1997).

Homandberg et al., "Exposure of Cartilage to a Fibronectin Fragment Amplifies Catabolic Processes while also Enhancing Anabolic Processes to Limit Damage", Journal of Orthopaedic Research, 16, pp. 237–246 (1998).

Homandberg et al., "Hyaluronic Acid Suppresses Fibronectin Fragment Mediated Cartilage Chondrolysis: I. In vitro", Osteoarthritis and Cartilage 5, pp. 309–319 (1997).

Homandberg et al., "Association of Proteoglycan Degradation with Catabolic Cytokine and Stromelysin Release from Cartilage Cultured with Fibronectin Fragments", 334:2, pp. 325–331 (1996).

Homandberg, "Potential Regulation of Cartilage Metabolism in Osteorthritis by Fibronectin Fragments".

Homandberg et al. "Fibronectin Fragment–Induced Cartilage Chondrolysis is Associated with Release of Catabolic Cytokines", Biochem J. 321, pp. 751–757, (Great Britain)(1997).

Homandberg et al., "Cartilage Damaging Activities of Fibronectin Fragments Derived from Cartilage and Synovial Fluid", Osteorthritis and Cartilage 6, pp. 231–244 (1998).

Homandberg, "Cartilage Chondrolysis by Fibronectin Fragments Causes Cleavage of Aggrecan at the Same Site as Found in Osteoarthritic Cartilage", Osteoarthritis and Cartilage 5, pp. 450–453 (1997).

Homandberg, "Fibronectin Fragment Mediated Cartilage Chondrolysis. I. Suppression by Anti–Oxidants", *BBA Biochimica et Biophysica Acta,* 1317, pp. 132–142 (1996).

Homandberg et al., "Fibronectin Fragment Mediated Cartilage Chondrolysis. II. Reparative Effects of Anti–Oxidants", *BBA Biochimica et Biophysica Acta,* 1317, pp. 143–148 (1996).

Ionescu et al. Heart Valve Replacement with the Ionescu–Shiley Pericardial Xenograft, The Journal of Thoracic and Cardiovascular Surgery, 73:1, pp. 31–42 (1977).

Kang et al., "Cultured Human Ankle and Knee Cartilage Differ in Susceptibility to Damage Mediated by Fibronectin Fragments", Journal of Orthopaedic Research, 16, pp. 551–556 (1998).

Lipman et al., "Xenografts of Articular Chondrocytes in the Nude Mouse", Calcif. Tissue Int., 35, pp. 767–772 (1983).

Oike et al., "Structural Analysis of Chick–embryo Cartilage Proteoglycan by Selective Degradation with Chondroitin Lyases (Chondroitinases) and Endo–β–D–Galactosidase (Keratanase)", Biochem. J., 191, pp. 193–207 (1980).

Williams et al., "Hyaluronic Acid Suppresses Fibronectin Fragment Mediated Cartilage Chondrolysis: II. In vivo", Osteoarthritis and Cartilage, 5, pp. 235–240 (1997).

Woodroof, "The Chemistry and Biology of Aldehyde Treated Tissue Heart Valve Xenografts".

Zhu et al., "Viscoelastic Shear Properties of Articular Cartilage and the Effects of Glycosidase Treatments", Journal of Orthopaedic Research, 11, pp. 771–781 (1993).

* cited by examiner

ALDEHYDE AND GLYCOSIDASE-TREATED SOFT AND BONE TISSUE XENOGRAFTS

RELATED APPLICATIONS

This application is a continuation in part of U.S. Ser. No. 09/036,171, filed Mar. 6, 1998, now U.S. Pat. No. 5,984,858, which is a continuation in part of application U.S. Ser. No. 08/483,256, filed Jun. 7, 1995, now U.S. Pat. No. 5,865,849.

FIELD OF THE INVENTION

The present invention relates to the field of treatment of defective human knee joints, heart valves, and bone and in particular, to replacement and repair of defective or damaged human knee joints, heart valves, and bone using a substantially immunologically compatible soft tissue or bone from a non-human animal.

BACKGROUND OF THE INVENTION

Soft Tissue

The term "soft tissue", as used herein, refers to cartilaginous structures, such as meniscus and articular cartilage; ligaments, such as anterior cruciate ligaments; tendons; and heart valves.

1. Meniscal Cartilage Soft Tissue

Specifically, the femoral condyles articulate with the surface plateaus of the tibia, through the cartilaginous medial and lateral menisci soft tissue, and all of these structures are held in place by various ligaments. The medial and lateral menisci are structures comprised of cells called fibrochondrocytes and an extracellular matrix of collagen and elastic fibers as well as a variety of proteoglycans. Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

Since joint cartilage in adults does not naturally regenerate to a significant degree once it is destroyed, damaged adult menisci have historically been treated by a variety of surgical interventions. Damaged menisci have been removed and replaced with prosthetic devices. An artificial knee joint having a rigid plastic femoral member and a metal tibial member is disclosed in U.S. Pat. No. 4,034,418. A number of meniscus prostheses have been devised which employ resilient materials such as silicone rubber or natural rubber, as in U.S. Pat. No. 4,344,193 and U.S. Pat. No. 4,502,161. Additional deformable, flexible resilient materials for a meniscus prosthesis such as collagen, tendon, or fibrocartilage are disclosed in U.S. Pat. No. 5,092,894 and U.S. Pat. No. 5,171,322. A cartilage replacement apparatus constructed of polyethylene plastic filled with small ball bearings or gelatinous fluid is described in U.S. Pat. No. 5,358,525. However, the known artificial prostheses have been unsatisfactory for treatment of damaged menisci, since they are deficient in the elastic, and therefore in the shock-absorbing, properties characteristic of natural menisci. Moreover, the known artificial devices have not proven able to withstand the forces inherent to routine knee joint function.

One of the present inventors provided improved prosthetic menisci in several of his earlier patents (U.S. Pat. No. 4,880,429; U.S. Pat. No. 5,007,934; U.S. Pat. No. 5,116,374; and U.S. Pat. No. 5,158,574). These patents generally disclose prosthetic menisci formulated from dry, porous matrices of processed natural fibers such as reconstituted cross-linked collagen, which optionally include glycosaminoglycan molecules. Generally, the source of collagen for these prosthetic menisci has been animal Achilles tendons or skin. The reconstitution process removes non-collagenous materials such as glycoproteins, proteoglycans, lipids, native glycosaminoglycans, and the like, which may confer additional elastic properties to the original tissue.

2. Articular Cartilage Soft Tissue

Articular cartilage soft tissue covers the ends of all bones that form articulating joints in humans and animals. Articular cartilage is made of fibrochondrocytes and an extracellular matrix of collagen fibers as well as a variety of proteoglycans. The cartilage acts in the joint as a mechanism for force distribution and as a lubricant in the area of contact between the bones. Without articular cartilage, stress concentration and friction would occur to the degree that the joint would not permit ease of motion. Loss of the articular cartilage usually leads to painful arthritis and decreased joint motion.

Damaged adult articular cartilage has historically been treated by a variety of surgical interventions including repair, replacement, or by excision. With repair or excision, regeneration of tissue may occur, although the tissue is usually temporary and inadequate to withstand the normal joint forces.

Replacement of articular cartilage usually has been by allografting (Sengupta et al. (1974) *J. Bone Suro*. 56B(1): 167–177; Rodrigo et al. (1978) *Clin Orth*. 134:342–349) by periosteal grafts (see, e.g., Engkvist (1979) *Scan J. Plast. Reconstr. Suro*. 13:361–369; Rubak (1982) *Acta Orthop. Scan*. 53:181–186) or with metal and/or plastic components (Rubash et al., eds. (1991) *Clin. Orth. Rel. Res*. 271:2–96). Allografting dead cartilage tissue has been tried for years with minimal success. This approach has been only partially successful over the long term due to the host's immunologic response to the graft, failures in the cryopreservation process, and failures of the attachment sites. Replacement of an entire joint surface with metal and plastic components has met excellent success for the older, more sedentary patients, but is generally considered insufficient for tolerating the impact of athletic activities, and has not been shown to restore normal joint mechanics.

In alternative prior art approaches, articular cartilage has been replaced with prostheses composed of bone and/or artificial materials. For example, U.S. Pat. No. 4,627,853 describes the use of demineralized allogenic or xenogeneic bone segments as replacements. The proper functioning of these replacements depends on the differential demineralization of the bone segments. U.S. Pat. No. 4,846,835 describes a grafting technique for transplantation of fibrochondrocytes to promote healing lesions in articular cartilage. U.S. Pat. No. 4,642,120 describes the use of gel-like compositions containing embryonal fibrochondrocytes. U.S. Pat. No. 5,306,311 describes a prosthetic articular cartilage which includes a dry, porous volume matrix adapted to have in vivo an outer contour substantially the same as that of natural articular cartilage.

Despite these developments, the replacement of articular cartilage soft tissue with structures consisting of permanent artificial materials generally has been less than satisfactory, and a structure suitable as articular cartilage and constructed from natural resorbable materials, or analogs thereof, has not been developed. Because the opposing articular cartilage of mammalian joints is so fragile, it will not withstand abrasive interfaces nor compliance variances from normal which eventually result from the implantation of prior art artificial cartilage. Additionally, joint forces are multiples of body weight which, in the case of the knee and hip, are typically encountered over a million cycles per year. Thus far, prior art permanent artificial cartilages have not been composed of materials having natural articular cartilage properties, nor have they been able to be positioned securely enough to withstand such routine forces.

3. Ligament Soft Tissue

Anterior cruciate ligament soft tissue of the knee (hereinafter the ACL) functions to resist anterior displacement of the tibia from the femur at all flexion positions. The ACL also resists hyperextension and contributes to rotational stability of the fully extended knee during internal and external tibial rotation. The ACL may play a role in proprioception. The ACL is made up of connective tissue structures composed of cells, water, collagen, proteoglycans, fibronectin, elastin, and other glycoproteins. Cyril Frank, M. D. et al., *Normal Ligament: Structure, Function, and Composition. Injury and Repair of the Musculoskeletal Soft Tissues*, 2:45–101. Structurally, the ACL attaches to a depression in the front of the intercondyloid eminence of the tibia extending postero-superiorly to the medial wall of the lateral femoral condyle.

The preferred treatment of damaged ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons are used for the reconstruction; placement of intraarticular hardware is required for ligament fixation; and anterior knee pain frequently occurs. Moreover, recent reviews of cruciate ligament reconstruction indicate an increased risk of degenerative arthritis with intraarticular ACL reconstruction in large groups of patients.

A second method of treating ACL injuries, referred to as "primary repair", involves suturing the torn structure back into place. Primary ACL repair has the potential advantages of a limited arthroscopic approach, minimal disruption of normal anatomy, and an out-patient procedure under a local anesthetic. The potential disadvantage of primary cruciate ligament repair is the perception that over the long term ACL repairs do not provide stability in a sufficient number of patients, and that subsequent reconstruction may be required at a later date. The success rate of anterior cruciate ligament repair has generally hovered in the 60% to 70% range.

4. Heart Valve Soft Tissue

Heart valves are composed of fibrochondrocytes and an extracellular matrix of collagen and elastic fibers, as well as a variety of proteoglycans. Various synthetic and tissue based materials (the latter either from the recipient organism or from a different organism within the same species) have been used for forming heart valve replacements. Each have their advantages and disadvantages.

In the case of synthetic heart valves, it may be possible to modify advantageously the properties of the heart valves by altering the monomers and/or the reaction conditions of the synthetic polymers. Synthetic heart valves may be associated with thromboembolism and mechanical failure, however. See U.S. Pat. No. 4,755,593.

Tissue based heart valves may demonstrate superior blood contacting properties relative to their synthetic counterparts. Tissue based heart valves also may be associated with inferior in vivo stability, however. See U.S. Pat. No. 4,755, 593.

Pericardial xenograft tissue valves have been introduced as alternatives to the synthetic and the tissue based valves described above. See Ionescu, M. I. et al., Heart Valve Replacement With The Ionescu-Shiley Pericardial Xenograft, J. Thorac. Cardiovas. Surg. 73; 31–42 (1977). Such valves may continue to have calcification and durability problems, however. See Morse, D, ed. *Guide To Prosthetic Heart Valves*, Springer-Verlag, New York, 225–232 (1985).

Accordingly, there is a need for mechanically durable, flexible heart valves replacements which are capable of contacting the blood and are stable in vivo.

Bone Tissue

Human bone, a hard connective tissue consisting of cells embedded in an extracellular matrix of mineralized ground substance and collagen fibers, (Stedman's Medical Dictionary, Williams & Wilkins, Baltimore, Md. (1995)), is the most frequently transplanted tissue in humans. J. M. Lane et al., Current Approaches to Experimental Bone Grafting, 18 Orthopedic Clinics of North America (2) 213 (1987). In the United States alone more than 100,000 bone graft or implant procedures are performed every year to repair or to replace osseous defects resulting from trauma, infection, congenital malformation, or malignancy. Id.

Bone grafts and implants are often formed of autologous bone. Id. Transplamtable autologous bone tissue for large defects, particularly in children, is often unavailable, however. Id. In addition, autologous bone transplantation may result in postoperative morbidity such as pain, hemorrhage, wound problems, cosmetic disability, infection or nerve damage at the donor site. Id. Further, difficulties in fabricating the desired functional shape from the transplanted autologous bone tissue may result in less than optimal filling of the bone defect. Id.

Xenografts

Much of the structure and many of the properties of original soft or bone tissues may be retained in transplants through use of heterograft or xenograft materials, that is, soft or bone tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, bum and other wound dressings is disclosed in U.S. Pat. No. 4,755, 593. Bovine, ovine, or porcine blood vessel xenografts are disclosed in WO 84/03036.

Once implanted in an individual, a xenograft provokes immunogenic reactions such as chronic and hyperacute rejection of the xenograft. In particular, bone xenografts may result in increased rates of fracture, resorption and nonunion secondary to immunologic rejection.

The term "chronic rejection", as used herein refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular matrices and/or extracellular components of the xenograft. For example, transplantation of soft tissue cartilage xenografts from nonprimate mammals (e.g., porcine or bovine origin) into humans is primarily prevented by the interaction between the IgG natural anti-Gal antibody present in the serum of humans with the carbohydrate structure Galα1-3Galβ1-4G1cNAc-R (α-galactosyl or α-gal epitope) expressed in the xenograft. K. R. Stone et al., Porcine and bovine cartilage transplants in cynomolgus monkey: I. A model for chronic xenograft rejection, 63 Transplantation 640–645 (1997); U. Galili et al., Porcine and bovine cartilage transplants in cynomolgus monkey: II. Changes in anti-Gal response during chronic rejection, 63 Transplantation 646–651 (1997). In chronic rejection, the immune system typically responds within one to two weeks of implantation of the xenograft.

In contrast with "chronic rejection", "hyper acute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system causing lysis of the vascular bed and stoppage of blood flow in the receiving individual within minutes to two to three hours.

The term "extracellular components", as used herein, refers to any extracellular water, collagen and elastic fibers, proteoglycans, fibronectin, elastin, and other glycoproteins, which are present in soft tissue; and to mineralized ground substance, bone and collagen fibers, which are present in bone tissue. Stedman's Medical Dictionary, Williams & Wilkins, Baltimore, Md. (1995).

Xenograft materials may be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the side chain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic soft or bone tissue xenograft for implantation into a human in need of soft or bone tissue repair or replacement. The invention further provides methods for processing xenogeneic soft or bone tissue with reduced immunogenicity but with substantially native elasticity and load-bearing capabilities for xenografting into humans.

As used herein, the term "xenograft" is synonymous with the term "heterograft" and refers to a graft transferred from an animal of one species to one of another species. Stedman's Medical Dictionary, Williams & Wilkins, Baltimore, Md. (1995).

As used herein, the term "xenogeneic", as in, for example, xenogeneic soft or bone tissue, refers to soft or bone tissue transferred from an animal of one species to one of another species. Id.

The methods of the invention, include, alone or in combination, treatment with radiation, one or more cycles of freezing and thawing, treatment with a chemical cross-linking agent, treatment with alcohol or ozonation. In addition to or in lieu of these methods, the methods of the invention include, alone or in combination, in any order, a cellular disruption treatment, glycosidase digestion of carbohydrate moieties of the xenograft, or treatment with proteoglycan-depleting factors (the proteoglycan-depleting factor treatment involving soft tissue xenografts only). Optionally, the glycosidase digestion or proteoglycan-depleting factor treatment can be followed by further treatments, such as, for example, treatment of carbohydrate moieties of the xenograft with capping molecules. After one or more of the above-described processing steps, the methods of the invention provide a xenograft having substantially the same mechanical properties as a native soft or bone tissue.

As used herein, the term "cellular disruption" as in, for example, cellular disruption treatment, refers to a treatment for killing cells.

As used herein, the term "capping molecule(s)", refers to molecule(s) which link with carbohydrate chains such that the xenograft is no longer recognized as foreign by the subject's immune system.

As used herein, the terms "to cap" or "capping", refer to linking a capping molecule such as a carbohydrate unit to the end of a carbohydrate chain, as in, for example, covalently linking a carbohydrate unit to surface carbohydrate moieties on the xenograft.

In one embodiment, the invention provides an article of manufacture comprising a substantially non-immunogenic soft or bone tissue xenograft for implantation into a human.

In another embodiment, the invention provides a method of preparing a soft or bone tissue xenograft for implantation into a human, which includes removing at least a portion of a soft or bone tissue from a non-human animal to provide a xenograft; washing the xenograft in water and alcohol; and subjecting the xenograft to at least one treatment selected from the group consisting of exposure to ultraviolet radiation, immersion in alcohol, ozonation, and freeze/thaw cycling, whereby the xenograft has substantially the same mechanical properties as a corresponding portion of a native soft or bone tissue.

As used herein, the term "portion", as in, for example, a portion of soft tissue, bone tissue, second surface carbohydrate moieties or proteoglycans, refers to all or less than all of the respective soft tissue, bone tissue, second surface carbohydrate moieties or proteoglycans of the xenograft.

In another embodiment, the invention provides a method of preparing a soft or bone tissue xenograft for implantation into a human, which includes removing at least a portion of a soft or bone tissue from a non-human animal to provide a xenograft; washing the xenograft in water and alcohol; subjecting the xenograft to a cellular disruption treatment; and digesting the xenograft with a glycosidase to remove first surface carbohydrate moieties, whereby the xenograft has substantially the same properties as a corresponding portion of a native soft or bone tissue.

As used herein, the term "first surface carbohydrate moiety (moieties)" refers to a terminal $\alpha$-galactosyl sugar at the non-reducing end of a carbohydrate chain.

In still other embodiments, this method can include additional steps such as, for example, treating second surface carbohydrate moieties on the xenograft with capping molecules to cap at least a portion of the second surface carbohydrate moieties, whereby the xenograft is substantially non-immunogenic.

As used herein, the term "second surface carbohydrate moiety (moieties)" refers to a N-acetyllactosamine residue at the non-reducing end of a carbohydrate chain, the residue being non-capped either naturally or as a result of prior cleavage of an α-galactosyl epitope.

In yet another embodiment, the invention provides a method of preparing a bone xenograft for implantation into a human, which includes removing at least a portion of a bone from a non-human animal to provide a xenograft; washing the xenograft in water and alcohol; and subjecting the xenograft to sterilization and cellular disruption treatments, whereby the xenograft has substantially the same properties as a corresponding portion of a native bone and is substantially non-immunogenic.

In a further embodiment, the invention provides a method of preparing a soft tissue xenograft for implantation into a human, which includes removing at least a portion of soft tissue from a non-human animal to provide a xenograft; washing the xenograft in water and alcohol; subjecting the xenograft to a cellular disruption treatment; and digesting the xenograft with a proteoglycan-depleting factor to remove at least a portion of the proteoglycans from the xenograft, whereby the xenograft has substantially the same mechanical properties as a corresponding portion of a native soft tissue and is substantially non-immunogenic.

In yet a further embodiment, the invention provides a method of preparing a xenograft formed of a soft or bone tissue for implantation into a human, which comprises removing at least a portion of the soft or bone tissue from a non-human animal to provide a xenograft; washing the xenograft in water and alcohol; subjecting the xenograft to a cellular disruption treatment; exposing the xenograft to an aldehyde in an amount ranging from about 0.01% to about 0.10%; and digesting the xenograft with a glycosidase to remove substantially first surface carbohydrate moieties from the xenograft, whereby the xenograft is substantially non-immunogenic and has substantially the same mechanical properties as the native soft or bone tissue.

In still yet further embodiments, the invention provides articles of manufacture including substantially non-immunogenic soft or bone tissue xenografts for implantation into humans produced by one or more of the above-identified methods of the invention.

In another embodiment, the invention provides a soft or bone tissue xenograft for implantation into a human which includes a portion of a soft or bone tissue from a non-human animal, wherein the portion has substantially no surface carbohydrate moieties which are susceptible to glycosidase digestion, and whereby the portion has substantially the same mechanical properties as a corresponding portion of a native soft or bone tissue.

In yet another embodiment, the invention provides a soft or bone tissue xenograft for implantation into a human which includes a portion of a soft or bone tissue from a non-human animal, wherein the portion includes extracellular components and substantially only dead cells, the extracellular components and dead cells having substantially no surface α-galactosyl moieties and having capping molecules linked to at least a portion of surface carbohydrate moieties. The portion of the soft or bone tissue is substantially non-immunogenic and has substantially the same mechanical properties as the native soft or bone tissue.

In a further embodiment, the invention provides a bone xenograft for implantation into a human which includes a sterilized, cellular disrupted portion of a bone from a non-human animal, whereby the portion is substantially non-immunogenic and has substantially the same mechanical properties as a corresponding portion of a native bone.

In still a further embodiment, the invention provides a soft tissue xenograft for implantation into a human which includes a portion of a soft tissue from a non-human animal, wherein the portion includes extracellular components and substantially only dead cells, the extracellular components having reduced proteoglycans. The portion of the soft tissue is substantially non-immunogenic and has substantially the same mechanical properties as the native soft tissue.

In yet still a further embodiment, the invention provides a xenograft formed of a soft or bone tissue for implantation into a human comprising a portion of the soft or bone tissue from a nonhuman animal, wherein the portion includes a plurality of extracellular components, a plurality of substantially only dead cells, and an aldehyde in an amount ranging from about 0.01% to about 0.10% crosslinking a plurality of proteins of the extracellular components, the extracellular components and the dead cells having substantially no surface carbohydrate moieties which are susceptible to glycosidase digestion, and whereby the portion is substantially non-immunogenic and has substantially the same mechanical properties as a corresponding portion of the native soft or bone tissue.

BRIEF DESCRIPTION OF THE DRAWINGS

The various features of the invention may be more fully understood from the following description when read together with the accompanying drawings.

DETAILED DESCRIPTION OF THE PREFERRED EMBODIMENTS

Figure 1:
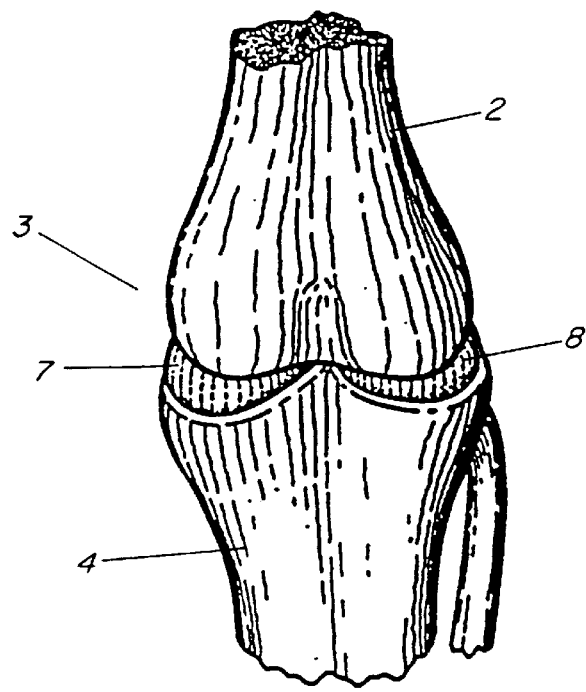
FIG. 1 shows a simplified diagrammatic representation of a human knee joint, with medial and lateral menisci in their native positions.
Figure 2:
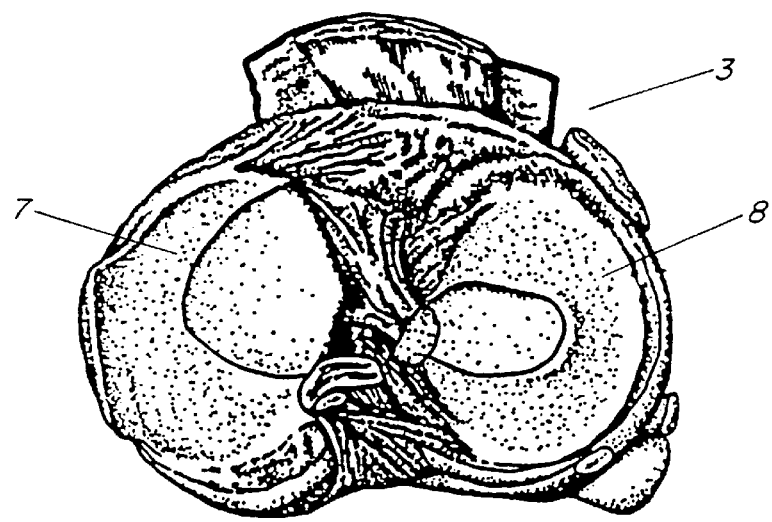
FIG. 2 is a diagrammatic representation of a cut-away view of a human knee joint, showing the medial and lateral menisci as they are positioned in vivo over the medial and lateral condyles of the tibia.

The present invention is directed against the chronic rejection of xenografts for implantation into humans. Accordingly, the soft or bone tissue xenograft produced in accordance with the method of the invention is substantially non-immunogenic, while generally maintaining the mechanical properties of a native soft or bone tissue.

While the soft or bone tissue may undergo some shrinkage during processing, a soft tissue xenograft prepared in accordance with the invention will have the general appearance of a native soft or bone tissue xenograft. For example, a medial meniscus xenograft prepared in accordance with the invention will have the general appearance of a native medial meniscus, and a lateral meniscus xenograft of the invention will have the general appearance of a native lateral meniscus. The soft or bone tissue xenograft may also be cut into segments, each of which may be implanted into a recipient as set forth below.

The invention provides, in one embodiment, a method for preparing or processing a xenogeneic soft or bone tissue for engraftment into humans. The soft or bone tissue may be harvested from any non-human animal to prepare the xenografts of the invention. Soft or bone tissue from transgenic non-human animals or from genetically altered non-human animals may also be used as xenografts in accordance with the present invention. Preferably, bovine, ovine, or porcine knee joints, and more preferably porcine knee joints, serve as sources of the medial and lateral menisci and articular cartilage soft tissue used to prepare the xenografts. Preferably, bovine and porcine joints, and more preferably porcine joints, serve as the source of the ligament soft tissue xenografts. Preferably, porcine peritoneum serves as the source of the soft tissue used to prepare the heart valve xenografts. Alternatively, porcine pericardium can be used to form the heart valve xenografts of the present invention. Preferably, bovine, ovine, or porcine bones, and more preferably porcine bones, serve as sources of the bone used to prepare the xenografts. More preferably, immature animal joints are the sources of the soft tissue, since the soft tissue of younger animals may be inherently more elastic and engraftable than that of older animals. More preferably, immature pig, calf or lamb bones are the sources of the bone, since the bone of younger animals consists of more cancellous bone and may be less brittle than that of older animals. Most preferably, the age of the source animal is between six and eighteen months at time of slaughter. Additionally, the patellar tendon, the anterior or posterior cruciate ligaments, the Achilles tendon or the hamstring tendons may be harvested from the animal source and used as a donor ligament.

In the first step of the method of the invention, an intact soft tissue is removed from a non-human animal. Medial or lateral meniscus are removed from the knee joints of the non-human animal. Articular cartilage are removed from any joint of the non-human animal. Ligaments and tendons, such as, for example, the Achilles tendon, as well as intact bone portions are also removed from non-human animals. Preferably soft tissue from a corresponding joint is used to make the soft tissue xenograft of the invention. For example, articular cartilage from a femuro-tibial (stifle) joint is used to make an articular cartilage xenograft for implantation into a knee. Similarly, articular cartilage from a donor animal's hip joint is used to make an articular cartilage xenograft for a human hip joint.

The source of the soft or bone tissues should be collected from freshly killed animals and preferably immediately placed in a suitable sterile isotonic or other tissue preserving solution. Harvesting of the soft and bone tissues should occur as soon as possible after slaughter of the animal and preferably should be performed in the cold, i.e., in the approximate range of about 5° C. to about 20° C., to minimize enzymatic degradation of the soft and bone tissues.

The soft and bone tissue portions are harvested in the cold, under strict sterile technique.

With respect to meniscal soft tissue, the joint is opened by first transecting the patellar tendon. The horns of the menisci are dissected free of adhering tissue. A small amount of bone representing a substantially cylindrical plug of approximately five millimeters in diameter by five millimeters in depth may be left attached to the horns. The meniscal synovial junction is carefully identified and freed from the meniscus tissue itself, thereby forming the xenograft.

With respect to articular cartilage soft tissue, a fine peel of articular cartilage with a small layer of subchondral bone is shaved from the donor joint to form the xenograft.

With respect to ligament soft tissue, the donor joint is opened by standard surgical technique. Preferably, the ligament is harvested with a block of bone attached to one or both ends, although in some forms of the invention the ligament alone is harvested. In one form of the invention, a block of bone representing a substantially cylindrical plug of approximately 9–10 mm in diameter by approximately 20–40 mm in length may be left attached to the ligament. The ligament is carefully identified and dissected free of adhering tissue, thereby forming the xenograft.

With respect to heart valve soft tissue, porcine peritoneum or pericardium is harvested to form the heart valve xenografts according to procedures known to those of ordinary skill in the art. See, for example, the peritoneum harvesting procedure discussed in U.S. Pat. No. 4,755,593 by Lauren.

With respect to the bone tissue, the harvested bone portion is cut up into strips or blocks and provided with and without cancellous bone attached to cortical bone.

The xenograft is then washed in about ten volumes of sterile cold water to remove residual blood proteins and water soluble materials. The xenograft is then immersed in alcohol at room temperature for about five minutes, to sterilize the tissue and to remove non-collagenous materials.

A meniscus soft tissue xenograft appears as a shiny "C"-shaped fibrous tissue, having generally a crescent-shaped principal surface on the top side (the "superior surface") and a generally crescent-shaped principal surface on the bottom side (the "inferior surface"), where the outer portions of the superior and inferior surfaces are joined by way of an outer lateral surface and the inner portions of the superior and inferior surfaces are joined by way of an inner lateral surface.

The articular cartilage soft tissue xenograft appears as a hyaline tissue supported on a bone substrate, having generally a spherical-shaped principal surface on the tip side (the "superior surface"), with the under surface of the bone (the "inferior surface") being rough.

After alcohol immersion, the xenograft may be directly implanted or may be subjected to at least one of the following treatments: radiation treatment, treatment with alcohol, ozonation, one or more cycles of freezing and thawing, and/or treatment with a chemical cross-linking agent. When more than one of these treatments is applied to the xenograft, the treatments may occur in any order.

In one embodiment of the method of the invention, the xenograft may be treated by exposure to ultraviolet radiation for about fifteen minutes or gamma radiation in an amount of about 0.5 to 3 MegaRad.

In another embodiment, the xenograft may be treated by again being placed in an alcohol solution. Any alcohol solution may be used to perform this treatment. Preferably, the xenograft is placed in a 70% solution of isopropanol at room temperature.

In still another embodiment, the xenograft may be subjected to ozonation.

In a further embodiment of the method of the invention, the xenograft may be treated by freeze/thaw cycling. For example, the xenograft may be frozen using any method of freezing, so long as the xenograft is completely frozen, i.e., no interior warm spots remain which contain unfrozen soft tissue. Preferably, the xenograft is dipped into liquid nitrogen for about five minutes to perform this step of the method. More preferably, the xenograft is frozen slowly by placing it in a freezer. In the next step of the freeze/thaw cycling treatment, the xenograft is thawed by immersion in an isotonic saline bath at room temperature (about 25° C.) for about ten minutes. No external heat or radiation source is used, in order to minimize fiber degradation.

In yet a further embodiment, the xenograft may optionally be exposed to a chemical agent to tan or crosslink the proteins within the extracellular components, to further diminish or reduce the immunogenic determinants present in the xenograft. Any tanning or crosslinking agent may be used for this treatment, and more than one crosslinking step may be performed or more than one crosslinking agent may be used in order to ensure complete crosslinking and thus optimally reduce the immunogenicity of the xenograft. For example, aldehydes such as glutaraldehyde, formaldehyde, adipic dialdehyde, and the like, may be used to crosslink the extracellular collagen of the xenograft in accordance with the method of the invention. Other suitable crosslinking agents include aliphatic and aromatic diamines, carbodiimides, diisocyanates, and the like.

When an aldehyde such as, for example, glutaraldehyde is used as the crosslinking agent, the xenograft may be placed in a buffered solution containing about 0.001% to about 5.0% glutaraldehyde and preferably, about 0.01 % to about 5.0% glutaraldehyde, and having a pH of about 7.4. More preferably about 0.01% to about 0.10% aldehyde, and most preferably about 0.01% to about 0.05% aldehyde is used. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from one to five days, and most preferably from three to five days.

Alternatively, the xenograft can be exposed to a crosslinking agent in a vapor form, including, but not limited to, a vaporized aldehyde crosslinking agent, such as, for example, vaporized formaldehyde or glutaraldehyde. The vaporized crosslinking agent can have a concentration and a pH and the xenograft can be exposed to the vaporized crosslinking agent for a period of time suitable to permit the crosslinking reaction to occur. For example, the xenograft can be exposed to vaporized crosslinking agent having a concentration of about 0.001% to about 5.0% and preferably, about 0.01% to about 5.0%, and a pH of about 7.4. More preferably, the xenograft is exposed to the aldehyde in an amount ranging from about 0.01% to about 0.10%, and most preferably to an aldehyde ranging in an amount from about 0.01% to about 0.05%. The xenograft is exposed to the aldehyde for a period of time which can be from one to fourteen days, and preferably from one to five days, and most preferably from three to five days. Exposure to vaporized crosslinking agent can result in reduced residual chemicals in the xenograft from the crosslinking agent exposure.

The crosslinking reaction should continue until the immunogenic determinants are substantially eliminated from the xenogeneic soft tissue, but the reaction should be terminated prior to significant alterations of the mechanical properties of the xenograft. When diamines are also used as crosslinking agents, the glutaraldehyde crosslinking should occur after the diamine crosslinking, so that any unreacted diamines are capped. After the crosslinking reactions have proceeded to completion as described above, the xenograft should be rinsed to remove residual chemicals, and 0.01–0.10 M glycine, and preferably, 0.01–0.05 M glycine may be added to cap any unreacted aldehyde groups which remain.

In addition to or in lieu of the above treatments, the xenograft can be subjected to a cellular disruption treatment to kill the xenograft's cells. Optionally, the cellular disruption treatment precedes or follows digestion of the xenograft with glycosidases to remove first surface carbohydrate moieties from the xenograft. With respect to the soft tissue xenograft, in addition or in lieu of the glycosidase treatment, either preceding or following the glycosidase treatment, the soft tissue xenograft is treated with proteoglycan-depleting factors. Further, the glycosidase and/or proteoglycan-depleting factor digestion (the latter for the soft tissue xenografts only) in turn is optionally followed by linkage with capping molecules such as fucosyl or n-acetyl glucosamine molecules to cap surface N-acetyllactosamine ends of carbohydrate chains of the xenograft.

In embodiments of this method of the invention, the xenograft is subjected to a cellular disruption treatment to kill the cells of the soft or bone tissue. Typically after surface carbohydrate moieties have been removed from living cells and the extracellular components, the living cells reexpress the surface carbohydrate moieties. Reexpression of antigenic moieties of a xenograft can provoke continued immunogenic rejection of the xenograft. In contrast, dead cells are unable to reexpress surface carbohydrate moieties. Removal of antigenic surface carbohydrate moieties from dead cells and the extracellular components of a xenograft substantially permanently eliminates antigenic surface carbohydrate moieties as a source of immunogenic rejection of the xenograft.

Accordingly, in the above-identified embodiments, the xenograft of the present invention is subjected to freeze/thaw cycling as discussed above to disrupt, i.e., to kill the cells of the soft or bone tissue. Alternatively, the xenograft of the present invention is treated with gamma radiation having an amount of 0.2 MegaRad up to about 3 MegaRad. Such radiation kills the soft or bone tissue cells and sterilizes the xenograft. Once killed, the soft or bone tissue cells are no longer able to reexpress antigenic surface carbohydrate moieties such α-gal epitopes which are factors in the immunogenic rejection of the transplanted xenografts.

Either before or after the soft or bone tissue cells are killed, in embodiments of the invention, the xenograft is subjected to in vitro digestion of the xenograft with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

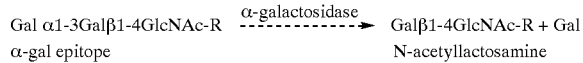

The N-acetyllactosamine residues are epitopes that are normally expressed on human and mammalian cells and thus are not immunogenic. The in vitro digestion of the xenograft with glycosidases is accomplished by various methods. For example, the xenograft can be soaked or incubated in a buffer solution containing glycosidase. In addition, the xenograft can be pierced to increase permeability, as further described below. Alternatively, a buffer solution containing the glycosidase can be forced under pressure into the xenograft via a pulsatile lavage process.

Elimination of the α-gal epitopes from the xenograft diminishes the immune response against the xenograft. The α-gal epitope is expressed in nonprimate mammals and in New World monkeys (monkeys of South America) as $1 \times 10^6 35 \times 10^6$ epitopes per cell, as well as on macromolecules such as proteoglycans of the extracellular components. U. Galili et al., Man, apes, and Old World monkeys differ from other mammals in the expression of -galactosyl epitopes on nucleated cells, 263 J. Biol. Chem. 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., Interaction between human natural anti-α-galactosyl immunoglobulin G and bacteria of the human flora, 56 Infect. Immun. 1730 (1988); R. M. Hamadeh et al., Human natural anti-Gal IgG regulates alternative complement pathway activation on bacterial surfaces, 89 J. Clin. Invest. 1223 (1992). Since nonprimate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., Interaction of the natural anti-Gal antibody with α-galactosyl epitopes: A major obstacle for xenotransplantation in humans, 14 Immunology Today 480 (1993); M. Sandrin et al., Anti-pig IgM antibodies in human serum react predominantly with Galα1-3Gal epitopes, 90 Proc. Natl. Acad. Sci. USA 11391 (1993); H. Good et al., Identification of carbohydrate structures which bind human anti-porcine antibodies: implications for discordant grafting in man. 24 Transplant. Proc. 559 (1992); B. H. Collins et al., Cardiac xenografts between primate species provide evidence for the importance of the α-galactosyl determinant in hyperacute rejection, 154 J. Immunol. 5500 (1995). Furthermore, xenotransplantation results in major activation of the immune system to produce increased amounts of high affinity anti-Gal. Accordingly, the substantial elimination of α-gal epitopes from cells and from extracellular components of the xenograft, and the prevention of reexpression of cellular α-gal epitopes can diminish the immune response against the xenograft associated with anti-Gal antibody binding with α-gal epitopes.

Further, the cartilage soft tissue xenografts of the present invention are particularly well suited to in vitro enzymatic elimination of the α-gal epitopes. In contrast to organs and other tissues, the cartilage extracellular components undergo extremely slow turnover. Moreover, once the cartilage cells, i.e., the fibrochondrocytes are killed, these cells are prevented from reexpressing the α-gal epitopes, as discussed above.

In addition, the soft or bone tissue xenografts may be treated with polyethylene glycol (PEG) prior to or concurrently with treatment with glycosidase. PEG acts as a carrier for the glycosidase by covalently bonding to the enzyme and to the collagen extracellular components. Further, PEG-treated xenografts have reduced immunogenicity.

With respect to the soft tissue xenografts, either before or after such tissue cells are killed, in embodiments of the invention, the xenograft is washed or digested with one or more different types of proteoglycan-depleting factors. The proteoglycan-depleting factor treatment can precede or follow glycosidase treatment. Proteoglycans such as glycosaminoglycans (GAGs) are interspersed either uniformly as individual molecules or within varying amounts within the extracellular components of the present invention's xenograft. The GAGs include mucopolysaccharide molecules such as chondroitin 4-sulfate, chondroitin 6-sulfate, keratan sulfate, dermatan sulfate, heparin sulfate, hyaluronic acid, and mixtures thereof. The proteoglycans including such GAGs contain attached carbohydrates such as α-gal epitopes. Such epitopes stimulate an immune response once the xenograft is transplanted, as discussed above. Washing or digesting the xenograft with the proteoglycan-depleting factor removes at least a portion of the proteoglycans and attached α-gal epitopes from the extracellular components of the xenograft, and thereby diminishes the immune response against the xenograft upon its transplantation. After the proteoglycan-depleting factor treatment and subsequent transplantation, natural tissue can repopulate the remaining collagen shell.

Non-limiting examples of the proteoglycan-depleting factors used in the present invention include proteoglycan-depleting enzymes such as chondroitinase ABC, hyaluronidase, chondroitin AC II lyase, keratanase, and trypsin.

Other proteoglycan-depleting factors used in the present invention include fragments of fibronectin. Homanberg et al. suggest that fibronectin fragments, such as the amino-terminal 29-kDa fragment, bind to the superficial surface of articular cartilage soft tissue and penetrate the cartilage to surround the cartilage cells. G. A. Homandberg et al., Fibronectin-fragment-induced cartilage chondrolysis is associated with release of catabolic cytokines, Biochem. J. (1997) 321, 751–757; G. A. Homandberg et al., Hyaluronic acid suppresses fibronectin fragment mediated cartilage chondrolysis: I. In vitro, Osteoarthritis and Cartilage (1997) 5, 309–319; G. A. Homandberg et al., High concentrations of fibronectin fragments cause short-term catabolic effects in cartilage tissue while lower concentrations cause continuous anabolic effects, Archives Of Biochemistry And Biophysics, Vol. 311, No. 2, June, pp. 213–218 (1994); G. A. Homandberg et al., Agents that block fibronectin fragment-mediated cartilage damage also promote repair, Inflammation Research 46 (1997) 467–471. At selected concentrations, Homanberg et al. further suggest that the addition of such fibronectin fragments to cartilage in vitro or in vivo results in the temporary suppression of proteoglycan synthesis and the enhancement of extracellular metalloproteinases which in turn cause a rapid proteoglycan loss from cartilage tissue. Id.

Other proteoglycan-depleting factors known to those of ordinary skill in the art are also possible for use with the present invention, however. The present invention's xenograft is treated with proteoglycan-depleting factor in an amount effective for removing at least a portion of the proteoglycans from the extracellular components of the xenograft. Preferably, the xenograft is treated with proteoglycan-depleting factor such as hyaluronidase in an amount ranging from about 1.0 TRU/ml to about 100.0 TRU/ml or proteoglycan-depleting factor such as chondroitinase ABC in an amount ranging from about 0.01 u/ml to about 2.0 u/ml or most preferably, in an amount ranging from about 1.0 ul/ml to about 2.0 $\mu$/ml. The xenograft can also be treated with proteoglycan-depleting factor such as fibronectin fragment, (e.g., amino terminal 29-kDa fibronectin fragment) in an amount ranging from about 0.01 $\mu$M to about 1.0 $\mu$M, and preferably in an amount ranging from about 0.1 $\mu$M to about 1.0 $\mu$M.

Following treatment with glycosidase or treatment with proteoglycan-depleting factors (the latter for soft tissue xenografts only), the remaining carbohydrate chains (e.g., glycosaminoglycans) of the xenograft are optionally treated with capping molecules to cap at least a portion of the remaining carbohydrate chains. Treatment with capping molecules is applicable to both glycosidase-treated and non-glycosidase-treated xenografts, however. For example, xenografts from knock out animals which may lack $\alpha$-gal epitopes may be treated with capping molecules to cap carbohydrate moieties on the xenograft, thereby reducing the xenograft's immunogenicity. Examples of capping molecules used in the present invention include fucosyl and N-acetyl glucosamine.

Prior to treatment, the outer surface of the xenograft (e.g., the outer lateral surface of meniscus soft tissue xenografts) optionally may be pierced to increase permeability to agents used to render the xenograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the xenograft. Piercing may also be performed with a laser. In one form of the invention, one or more straight lines of punctures about three millimeters apart are established circumferentially in the outer lateral surface of the xenograft.

Prior to implantation, the soft or bone tissue xenograft of the invention may be treated with limited digestion by proteolytic enzymes such as ficin or trypsin to increase tissue flexibility, or coated with anticalcification agents, antithrombotic coatings, antibiotics, growth factors, or other drugs which may enhance the incorporation of the xenograft into the recipient joint. The soft tissue xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

Further, the bone xenograft of the invention can be treated with an osteoinductive factor in an effective amount to stimulate the conversion of soft tissue cells to osseous tissue formers. Alternatively or additionally, the osteoinductive factor can be administered directly to the target defect. As used herein, the term "osteoinductive factor" refers to a protein which stimulates the differentiation of uncommitted connective tissue cells into bone-forming cells. J. M. Lane et al., Current Approaches to Experimental Bone Grafting, 18 Orthopedic Clinics of North America (2) 214 (1987). Methods of preparing and administering the osteoinductive factor to a graft or to the target defect are known in the prior art such as, for example, Sharon Stevenson, D. V. M., Ph.D., et al., The Effect of Osteogenic (A Bone Morphogenetic Protein) on the Formation of Bone in Orthotopic Segmental Defects in Rats, 76, A. The Journal of Bone And Joint Surgery No. 11, 1676–1687 (1994) and John E. Feighan, et al., Induction of Bone by a Demineralized Bone Matrix Gel: A Study in a Rat Femoral Defect Model, 13 Journal of Orthopaedic Research 881–889 (1995). For example, osteoinductive factor in the form of a gel, in the presence of a synthetic carrier, such as a hydroxyapatite ceramic cylinder, or using a carrier, such as polyethylene glycol (PEG) or glycerol, or a buffer, such as phosphate, and/or any combination of the above can be administered to the defect site and/or used to impregnate the xenograft.

The osteoinductive factor is added to the interstices of the xenograft and/or to the defect site in an amount effective to induce bone formation. For example, doses of about 10 mg to about 200 mg of osteoinductive factor can be added. Examples of osteoinductive factors which can be used in the present invention include bone morphogenic proteins (BMP) and associated non-collagenous proteins (NCP). Such osteoinductive factors are commercially available from, for example, Creative Biomolecules, Inc., Hopkington, Mass.

The bone xenograft of the invention also can be treated with a demineralization agent in an effective amount to remove substantially minerals such as, for example, calcium from the extracellular matrix of the xenograft. For example, the xenograft of the invention can be soaked in a solution containing demineralization agents, such as, hydrochloric acid, and other demineralization agents known to those of ordinary skill in the art, at a predetermined concentration to demineralize substantially the xenograft of the invention. Once the minerals are removed from the xenograft, a porous volume matrix is formed with pores ranging in size from about 50 microns to about 500 microns. It is theorized that the collagen of demineralized extracellular bone matrix serves as an osteoconductive scaffolding and facilitates the migration of bone forming components once bone graft is implanted. J. M. Lane et al., Current Approaches to Experimental Bone Grafting, 18 Orthopedic Clinics of North America (2) 220 (1987). It is further theorized that demineralized bone possesses greater osteoinductive activity than, for example, autologous bone, because bone mineral impedes the release of osteoinductive proteins from extracellular bone matrix. Id. at 218. According to this theory, demineralization enlarges the access of surrounding responsive cells to osteoinductive proteins and augments the potential of the osteoinductive proteins. Such demineralization agents are commercially available from, for example, Sigma, Inc., St. Louis, Mo.

In addition, a binding agent can be added into the bone xenograft of the present invention. As used herein, a binding agent is an adhesion molecule, or adhesive portion or analog thereof, which aids in bone formation by providing a tacky surface to which bone forming cells can stick. The binding agent is added in an effective amount to facilitate the attachment of mesenchymal and other differentiated bone forming cells to the extracellular matrix of the bone xenograft. Examples of binding agents useful in the present invention include bone cement; fibrin glue; mussel glue, such as mussel glue containing bioadhesive polyphenolic proteins derived from several species of the mussel genus Mytilus (see e.g., U.S. Pat. No. 4,585,585); chondronectin; osteonectin; and fibronectin and arginine-glycine-aspartic acid (RGD) peptide (see e.g., U.S. Pat. No. 5,681,353), a portion of which can be conjugated to, for example, chondroitin sulfate, and other binding agents known to those persons of ordinary skill in the art. Such binding agents are commercially available from, for example, Telios Pharmaceuticals, Inc., San Diego, Calif.

The soft or bone tissue xenograft of the invention, or a segment thereof, may be implanted into damaged human joints by those of skill in the art using known arthroscopic surgical techniques. Specific instruments for performing arthroscopic techniques are known to those of skill in the art, which ensure accurate and reproducible placement of soft tissue implants.

Meniscus Cartilage Soft Tissue Xenograft Implantation

For meniscal cartilage replacement to succeed, the following goals are preferably accomplished:

1. The torn fragmented pieces of native meniscal cartilage must be removed.
2. The attachment sites for the meniscal horns must be anatomically placed.
3. The periphery of the meniscal implant must be attached securely enough to permit axial and rotational loads.
4. The surrounding capsule and ligaments of the knee joint must be neither excessively violated nor constrained by the fixation technique. The method of meniscal implantation described in detail below is derived from K. R. Stone, et al., *Arthroscopy: The Journal of Arthroscopic and Related Surgery* 9, 234–237 (1993); other methods of meniscal implantation may also be employed to use the xenogeneic meniscal xenografts of the present invention.

Figure 3:
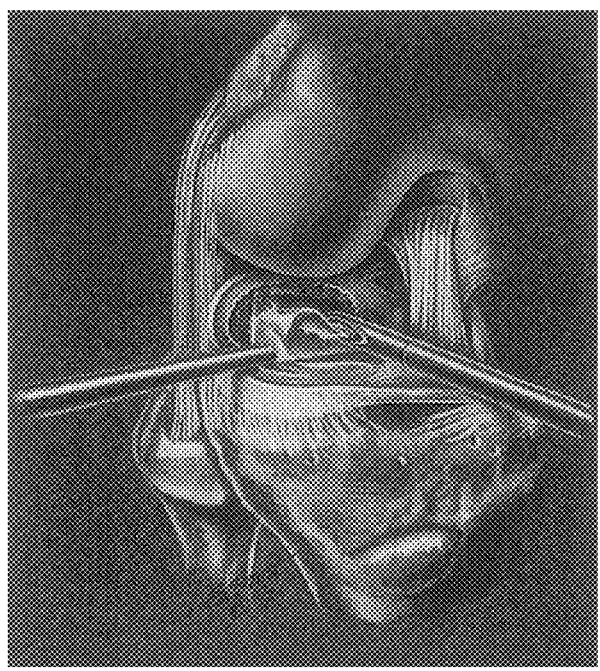
FIG. 3 is a diagrammatic representation of resection of a torn lateral meniscus of a human knee, and preparation of the knee for receipt of a meniscal implant.

Initially, complete diagnostic arthroscopy of the knee joint is accomplished using known methods. If ACL surgery is to be performed simultaneously, the femoral and tibial tunnels for the cruciate reconstruction should be drilled first. The torn portion of the meniscal cartilage is evaluated. If meniscal repair cannot be accomplished due to severity of the tear or poor quality of the tissue, then preparation of the meniscal rim is undertaken by removing the torn portions of the cartilaginous tissue (FIG. 3). When the entire human meniscus is to be replaced by a xenogeneic meniscus xenograft of the invention, nearly all of the human meniscus is removed. Additionally, for replacement of the entire human meniscus with a xenogeneic meniscus xenograft of the invention, resection of the human meniscal horns and preparation of bony tunnels to accept bone plugs may be required. When only a portion of the human meniscus is to be replaced with a segment of the xenogeneic meniscus xenograft of the invention, only the damaged portions are removed, preserving the peripheral rim and horns for attachment of the xenogeneic meniscus xenograft segment. If absolutely no human meniscal rim is present, then partial replacement of the meniscus should not be performed. If the joint is excessively tight, a joint distractor may be applied or the medial collateral ligament may be partially released.

Figure 4:
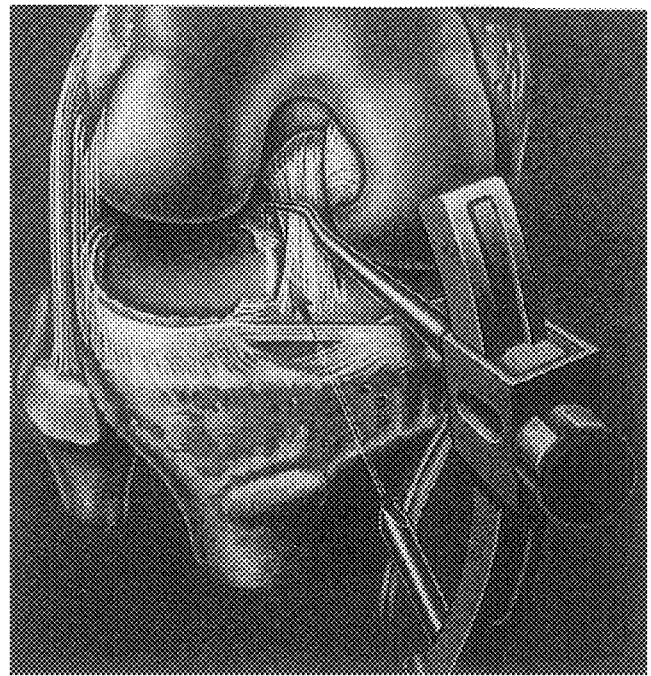
FIG. 4 is a diagrammatic representation the preferred drill guide placement for posterior lateral meniscal horn insertion into a human knee.
Figure 5:
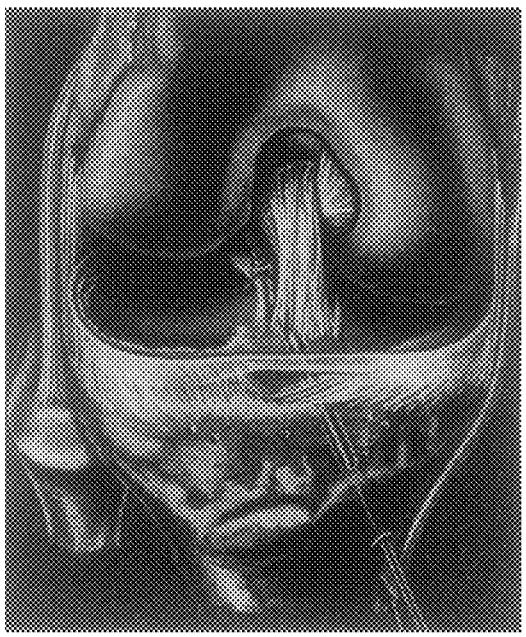
FIG. 5 is a diagrammatic representation of a cannulated drill overdrilling guide wire at the posterior lateral meniscal horn insertion into a human knee.

For medial or lateral meniscal replacement, the arthroscope is placed in the mid-lateral or anterior lateral portal and the tibial guide is placed through the anterior medial portal. The tip of the guide is brought first to the posterior horn of the meniscus. It should be noted that the posteromedial horn inserts on the posterior slope of the tibial eminence. A (frill pin is then brought from the anterior medial side of the tibial tuberosity to the posterior horn insertion (FIG. 4). The pin placement can be confirmed by passing the arthroscope through the intercondylar notch and viewing the exit site of the pin. Extreme care must be undertaken to avoid penetration through the posterior capsule of the knee, endangering the neurovascular bundle. When the pin position is confirmed, the pin is then overdrilled with a 4.5-mm cannulated drill bit with the option of a drill stop to prevent posterior capsular penetration (FIG. 5). The bit is left in place and used as a tunnel for passage of a suture passer with a suture such as a #2 EthibondTM suture available from Johnson & Johnson. The suture is passed up the bore of the drill bit, the drill bit removed, and the suture left in place.

Figure 6:
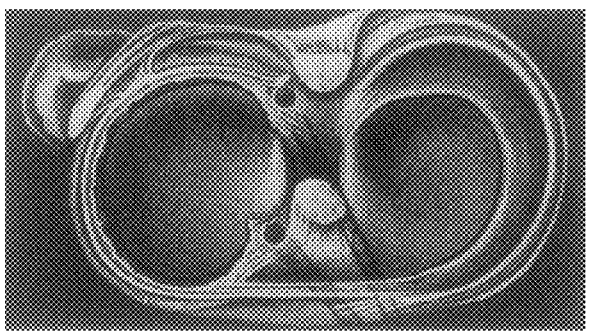
FIG. 6 is a diagrammatic representation of the appearance of a human knee with posterior and anterior drill holes for meniscal horn insertion.

The anterior medial meniscus insertion point in humans varies considerably, most often being found anterior to the medial tibial eminence. The anterior horn of the lateral meniscus inserts just posterior to the anterior cruciate ligament. An anterior drill hole is made by first identifying the insertion point of the anterior horn of the lateral meniscus, by placing the tip of the drill guide so that a relatively vertical hole will be made (FIG. 6). The drill pin is placed, then the cannulated drill bit is used to overdrill the drill pin placement to form the anterior drill hole. A suture passer is placed in the anterior drill hole. Alternatively, the anterior horn of the medial meniscus is affixed with a suture anchor directly to bone as opposed to a drill hole.

Before the suture is grasped from the anterior and posterior drill holes, the anterior portal is widened to approximately 2 cm. The suture grasper is then passed through the widened portal, and both the anterior and the posterior sutures brought out simultaneously. This technique prevents the sutures from becoming entangled in two different planes of the fat pad and capsular tissue.

Figure 7:
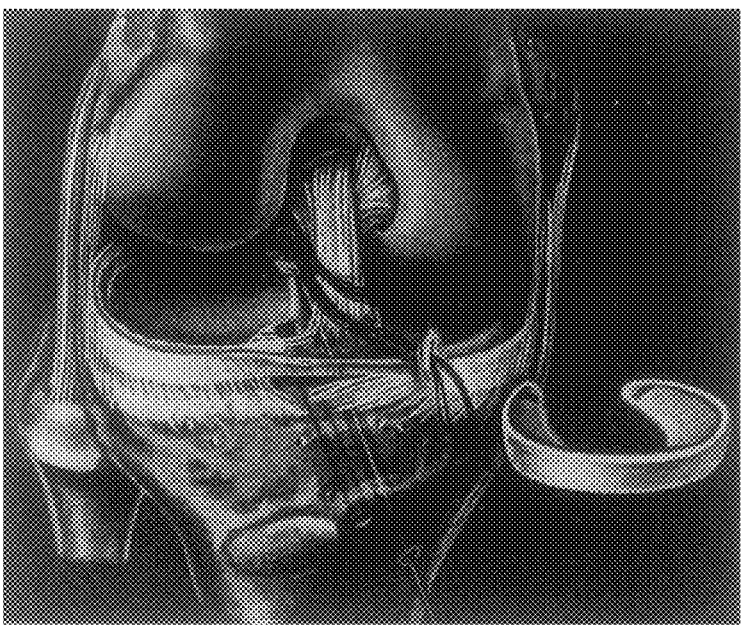
FIG. 7 is a diagrammatic representation of the preferred suture passer placement for pulling a meniscal implant into a human knee joint.
Figure 8:
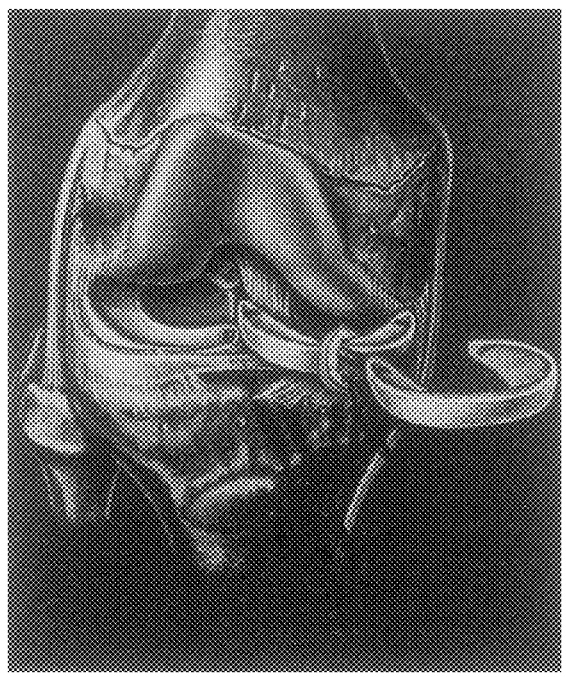
FIG. 8 is a diagrammatic representation of the appearance of a human knee containing a meniscal implant during the insertion stage.

The implant is now brought onto the field. Two horizontal mattress sutures, for example, #2-0 EthibondT sutures or the like, are placed through each horn of the xenogeneic meniscus xenograft with the free ends exiting the inferior surface (FIG. 7). The two posterior sutures are then drawn through the knee and out the posterior tibial tunnel (FIG. 8). If viewing from a mid-lateral portal, the anterolateral portal can be used for probe insertion to push the implant medially into place through a 1-inch incision. No insertion cannula is required. The anterior sutures are then similarly passed. The horn sutures are then tied over the anterior tibial bony bridge.

Figure 9:
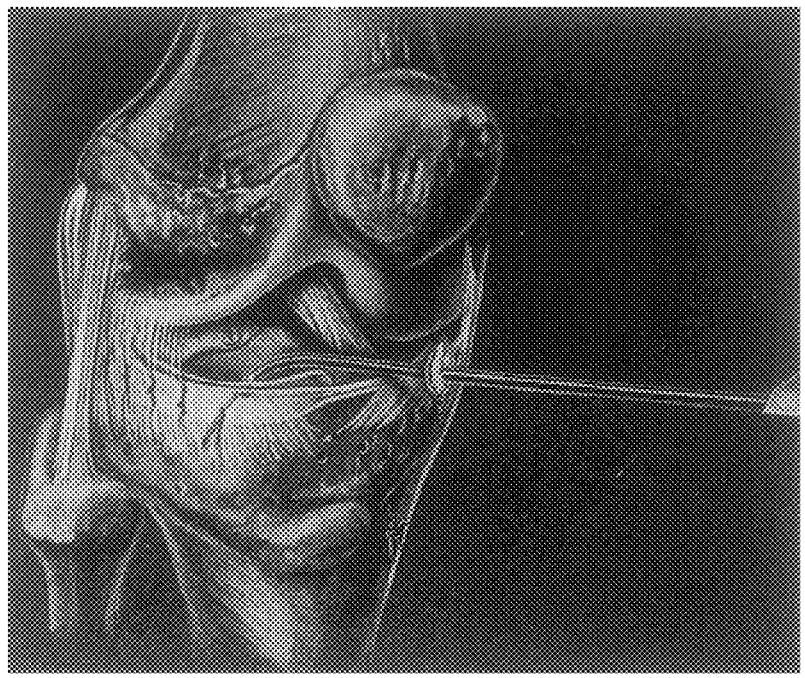
FIG. 9 is a diagrammatic representation of the appearance of a human knee containing a meniscal implant with zone-specific meniscal repair sutures in place for final tying of the meniscal repair sutures.
Figure 10:
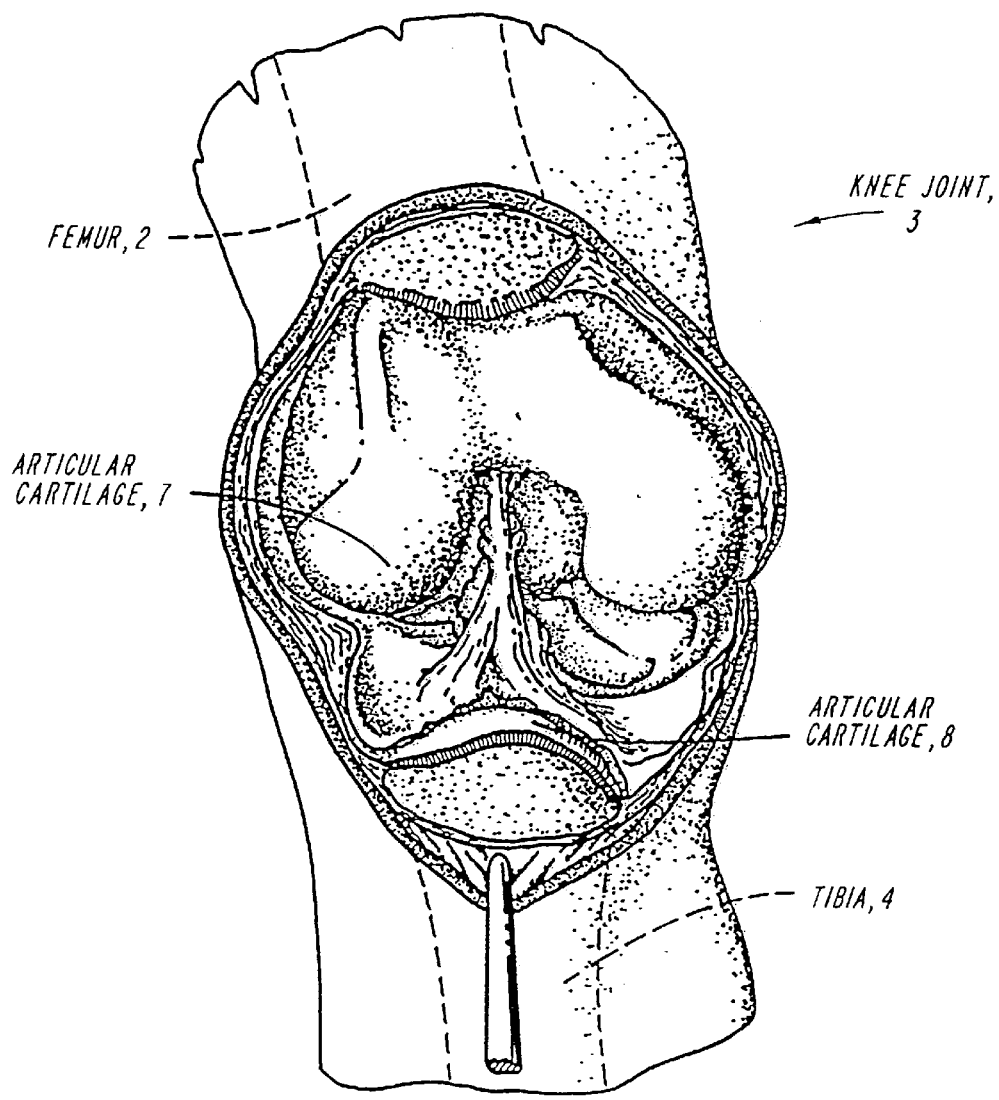
FIG. 10 is shows a simplified diagrammatic representation of a human knee joint 3, showing the normal positioning of articular cartilage 7 on the articulating end of femur 2 and articular cartilage 8 on the articulating end of tibia 4.

Next, zone specific meniscal repair cannulae are brought into place. For medial insertions, a posterior medial vertical incision is made one third of the distance from the back of the knee for protection of the saphenous nerve and for retrieval of the inside-out meniscal repair needles. A second vertical incision is usually required further anteriorly, next to the anterior medial arthroscopy portal, to capture the anterior exiting needles. Through these two incisions, the suture needles can be captured and the knots placed directly over the capsule (FIG. 9).

When using the meniscal repair needles, the posterior cannulae should be used first, with the sutures placed vertically and evenly spaced. The repair should proceed from posterior to anterior so that a buckle is not produced within the xenograft. Each knot is tied as it is placed to avoid the chance of suture tangling. The knots are spaced approximately 4 mm apart. The knee is cycled through several complete ranges of motion of ensure that the xenograft moves smoothly without impingement.

When performing a lateral meniscal replacement, the medial portal is suitable for xenograft insertion. This may require excision of the ligamentous mucosa and removal of a portion of the fat pad. The drill guide for the posterior horn of the lateral meniscus is inserted through the anteromedial portal. The posterior slope of the lateral tibial spine must be identified for accurate meniscal horn insertion. The anterior horn inserts on the anterior slope of the lateral tibial spine in approximation to the lateral aspect of the anterior cruciate ligament. The advantage of drilling these holes from the medial side is that the tunnel divergence will be greater, providing a larger bony bridge between the horn insertions. The remainder of the insertion technique remains the same, except that great care should be taken to protect the neurovascular bundle when suturing the posterior horn. Accessing posterolateral exposure is necessary to safeguard the common peroneal nerve and to expose the lateral capsule. If there is any doubt about the suture placement, open posterior horn suturing should be performed in the standard fashion. Alternatively, meniscus and/or stabilization devices such as arrows or staples can be used instead of sutures. Stabilization arrows manufactured by Bionix, Inc., Malvern, Pa., are non-limiting examples of such stabilization arrows. Other stabilization devices known to those of ordinary skill in the art can also be used.

Routine skin closure and dressings are applied. Thirty milliliters of 0.5% Marcaine (Astra) with epinephrine may be instilled if desired. A postoperative hinged knee brace may be applied with the range of motion limited to 30° of extension and 90° of flexion.

Articular Cartilage Soft Tissue Xenograft Implantation

The underlying bone bed of the recipient joint is prepared with a bone burr to produce a cancellous bleeding bed. Grafting can involve either the entire articular surface or a portion of the articular surface. The substantially non-immunogenic articular cartilage xenograft of the invention is applied to the recipient joint as a cover, which is held in place by one or more suture anchors, absorbable pins, screws, staples, and the like. A fibrin clot may also be used to hold the substantially non-immunogenic articular cartilage xenograft in place.

Ligament Soft Tissue Xenograft Implantation

The irreparably damaged ligament is removed with a surgical shaver. The anatomic insertion sites for the ligament are identified and drilled to accommodate a bone plug. The size of the bone plug can be about 9–10 mm in width by about 9–10 mm in depth by about 20–40 mm in length. The xenogeneic ligament is brought through the drill holes and affixed with interference screws. Routine closure is performed.

This invention is further illustrated by the following Examples which should not be construed as limiting. The contents of all references and published patents and patent applications cited throughout the application are hereby incorporated by reference.

Heart Valve Soft Tissue Xenograft Implantation

The heart valve xenograft of the invention, or a segment thereof, may be formed of porcine peritoneum or pericardium and may be implanted to replace and/or to repair damaged heart valves by those of skill in the art using known techniques. Such techniques are performed with specific instruments which insure accurate and reproducible placement of the implants and which are known to those of ordinary skill in the art.

Bone Tissue Xenograft Implantation

The bone xenograft of the invention, or a segment thereof, may be implanted into damaged human joints by those of skill in the art using known arthroscopic surgical techniques. Holes in bones are manually packed with bone according to standard surgical techniques. Specific instruments for performing surgical techniques, which ensure accurate and reproducible placement of bone implants are known to those of skill in the art.

EXAMPLE 1

Assay For α-Gal Epitopes' Elimination From Soft Tissue By α-Galactosidase

In this example, an ELISA assay for assessing the elimination of α-gal epitopes from soft tissue is conducted.

A monoclonal anti-Gal antibody (designated M86) which is highly specific for α-gal epitopes on glycoproteins is produced by fusion of splenocytes from anti-Gal producing knock-out mice for α 1,3 galactosyltransferase, and a mouse hybridoma fusion partner.

Figure 11:
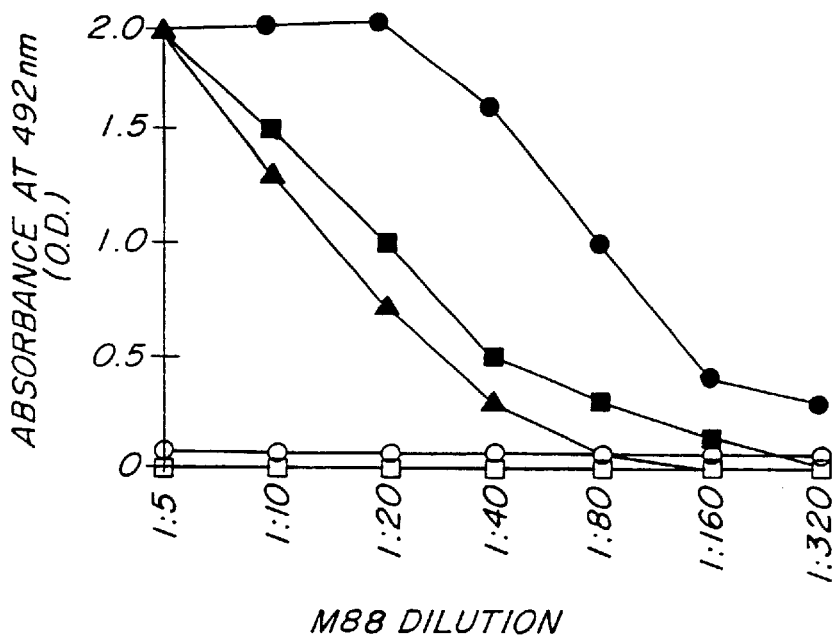
FIG. 11 is a graphical representation of the specificity of monoclonal anti-Gal antibodies for α-galactosyl epitopes on bovine serum albumin (BSA), bovine thyroglobulin, mouse laminin, Galβ1-4 G1cNAc-BSA (N-acetyllactosamine-BSA), Galα1-4Galβ1-4G1cNAc-BSA (P1 antigen linked to BSA), and human thyroglobulin or human laminin.

The specificity of M86 for α-gal epitopes on glycoproteins is illustrated in FIG. 11. M86 binds to synthetic α-gal epitopes linked to ●-bovine serum albumin (BSA), to ▲-bovine thyroglobulin which has 11 α-gal epitopes, R. G. Spiro et al., Occurrence of α-D-galactosyl residues in the thyroglobulin from several species. Localization in the saccharide chains of complex carbohydrates, 259 J. Biol. Chem. 9858 (1984); or to ■-mouse laminin which has 50 α-gal epitopes, R. G. Arumugham et al., Structure of the asparagine-linked sugar chains of laminin. 883 Biochem. Biophys. Acta 112 (1986); but not to □-human thyroglobulin or human laminin, O-Galβ-4 G1cNAc-BSA (N-acetyllactosamine-BSA) and Galα1-4Galβ1-4G1cNAc-BSA (P1 antigen linked to BSA), all of which completely lack α-gal epitopes. Binding is measured at different dilutions of the M86 tissue culture medium.

Once the M86 antibody is isolated, the monoclonal antibody is diluted from about 1:20 to about 1:160, and preferably diluted from about 1:50 to about 1:130. The antibody is incubated for a predetermined period of time ranging between about 5 hr to about 24 hr, at a predetermined temperature ranging from about 3° C. to about 8° C. The antibody is maintained in constant rotation with fragments of soft tissue about 5 μm to about 100 μm in size, and more preferably with soft tissue fragments ranging from about 10 μm to about 50 μm in size, at various soft tissue concentrations ranging from about 200 mg/ml to about 1.5 mg/ml. Subsequently, the soft tissue fragments are removed by centrifugation at centrifugation rate ranging from about 20,000×g to about 50,000×g. The proportion of M86 bound to the soft tissue is assessed by measuring the remaining M86 activity in the supernatant, in ELISA with α-gal-BSA as described in the prior art in, for example, U. Galili et al., Porcine and bovine cartilage transplants in cynomolgus monkey: II. Changes in anti-Gal response during chronic rejection, 63 Transplantation 645–651 (1997). The extent of binding of M86 to the soft tissue is defined as a percentage inhibition of subsequent binding to α-gal-BSA. There is a direct relationship between the amount of α-gal epitopes in the soft tissue and the proportion of M86 complexed with the soft tissue fragments, thus removed from the supernatant (i.e., percentage inhibition).

Figure 12:
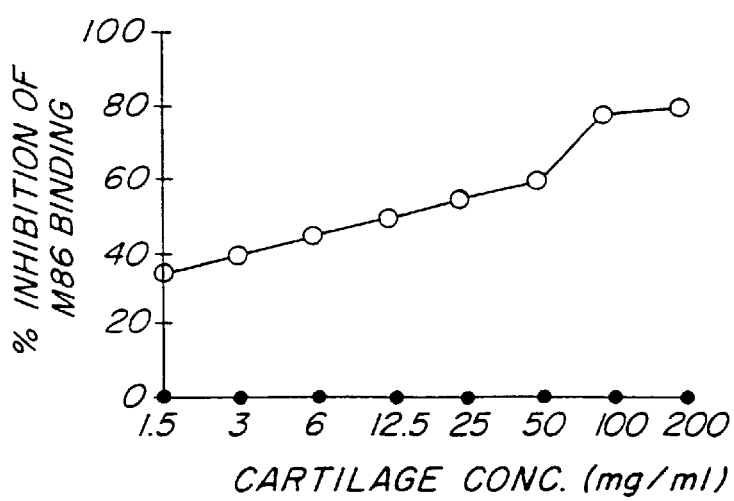
FIG. 12 is a graphical representation of α-galactosyl epitope elimination from α-galactosidase treated meniscal cartilage.

An example of the assay is shown in FIG. 12. Fragments of homogenized meniscus cartilage (○) or meniscus cartilage (●) treated with α-galactosidase are incubated with the M86 monoclonal antibody (diluted 1:100) for 20 hr at 4° C. Subsequently, the meniscus cartilage fragments are removed by centrifugation at 35,000×g and the remaining M86 in the supernatant is assessed in ELISA with α-gal-BSA as solid phase antigen. FIG. 12 shows that treatment of the meniscus cartilage with 200 U/ml α-galactosidase for 4 hour at 30° C. followed by five washes with phosphate-buffered solution (PBS) completely eliminates the α-gal epitopes. Thus, since there is no inhibition of subsequent M86 binding to α-gal-BSA even at a high meniscus cartilage fragment concentration of 200 mg/ml.

EXAMPLE 2

Assessment Of Primate Response To Implanted Porcine Meniscus Cartilage, Articular Cartilage, Ligament And Heart Valve Soft Tissue Xenografts Treated With α-Galactosidase In this example, porcine meniscus cartilage, articular cartilage, ligament, and peritoneum heart valve soft tissue implants are treated with α-galactosidase to eliminate α-galactosyl epitopes, the implants are transplanted into cynomolgus monkeys, and the primate response to the soft tissue implants is assessed.

Porcine stifle joints are sterilely prepared and meniscus cartilage and articular cartilage and other surrounding attached soft tissues surgically removed. Porcine peritoneum is also harvested for forming heat valve xenografts and adherent fatty and/or muscular tissues surgically removed. The meniscus cartilage, articular cartilage and heart valve soft tissue specimens are washed for at least five minutes with an alcohol, such as ethanol or isopropanol, to remove synovial fluid and lipid soluble contaminants. The meniscus cartilage, articular cartilage and heart valve soft tissue specimens are frozen at a temperature ranging from about $-35°$ C. to about $-90°$ C., and preferably at a temperature up to about $-70°$ C., to disrupt, that, is to kill, the specimens' fibrochondrocytes.

Porcine stifle joints are also sterilely prepared and ligaments, each with a block of bone attached to one or both ends, are removed in the cold, under strict sterile technique. Each of the blocks of bone represents a substantially cylindrical plug of approximately 9 mm in diameter by about 40 mm in length. Each ligament soft tissue specimen is carefully identified and dissected free of adhering tissue, thereby forming the xenograft. The ligament soft tissue xenograft specimens are then washed for at least five minutes with an alcohol, such as ethanol or isopropanol, to remove synovial fluid and lipid soluble contaminants. Subsequently, the specimens are frozen at a temperature of about $-70°$ C. to disrupt, that is, to kill, the ligament specimens' cells.

Each meniscus cartilage, articular cartilage, heart valve and ligament soft tissue xenograft specimen is cut into two portions. Each first portion is immersed in a buffer solution containing α-galactosidase at a predetermined concentration. The specimens are allowed to incubate in the buffer solutions for a predetermined time period at a predetermined temperature. Each second portion is incubated under similar conditions as the corresponding first portion in a buffer solution in the absence of α-galactosidase and serves as the control.

At the end of the incubation, the soft tissue xenograft specimens are washed under conditions which allow the enzyme to diffuse out. Assays are performed to confirm the complete removal of the α-gal epitopes.

Each meniscus cartilage soft tissue xenograft specimen is implanted in the supra patellar pouch of six cynomolgus monkeys. With the animals under general inhalation anesthesia, an incision of about 1 cm is made directly into the supra patellar pouch at the superior medial border of the patella extending proximally. A piece of the porcine cartilage soft tissue of about 0.5 cm to about 1 cm in length is placed into the pouch with a single nylon stitch as a marking tag.

The articular cartilage xenograft specimens are implanted in the supra patellar pouch of six cynomolgus monkeys substantially following the above-identified implantation procedure.

The porcine peritoneum is formed into heart valves and the heart valve xenograft specimens are implanted in the six cynomolgus monkeys according to heart valve implantation procedures known to those of ordinary skill in the art.

The ligament soft tissue xenograft specimens are implanted in six cynomolgus monkeys using the following implantation procedure. With the animals under general inhalation anesthesia, the anatomic insertion sites for the xenogeneic ligament are identified and drilled to accommodate a substantially 9 mm in diameter by 40 mm in length bone plug. The xenogeneic ligament is brought through the drill holes and affixed with interference screws.

The implantation procedures are performed under sterile surgical technique., and the wounds are closed with 3-0 vicryl or a suitable equivalent known to those of ordinary skill in the art. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-soft tissue antibodies (i.e., antibodies binding to soft tissue antigens other than the α-gal epitopes) in serum samples from the transplanted monkeys. At least two ml blood samples are drawn from the transplanted monkeys on the day of implant surgery and at periodic (e.g., two week) intervals post-transplantation. The blood samples are centrifuged and the serum samples are frozen and evaluated for the anti-Gal and other non-anti-Gal anti-soft tissue antibody activity.

Anti-Gal activity is determined in the serum samples in ELISA with α-gal-BSA as solid phase antigen, according to methods known in the prior art, such as, for example, the methods described in Galili et al., Porcine and bovine cartilage transplants in cynomolgus monkey: II. Changes in anti-Gal response during chronic rejection, 63 Transplantation 645–651 (1997).

Assays are conducted to determine whether α-galactosidase treated xenografts induce the formation of anti-soft tissue antibodies. For measuring anti-soft tissue antibody activity, ELISA assays are performed according to methods known in the prior art, such as, for example, the methods described in K. R. Stone et al., Porcine and bovine cartilage transplants in cynomolgus monkey: I. A model for chronic xenograft rejection, 63 Transplantation 640–645 (1997).

The soft tissue xenograft specimens are optionally explanted at one to two months post-transplantation, sectioned and stained for histological evaluation of inflammatory infiltrates. Post-transplantation changes in anti-Gal and other anti-cartilage soft tissue antibody activities are correlated with the inflammatory histologic characteristics (i.e., granulocytes or mononuclear cell infiltrates) within the explanted soft tissue, one to two months post-transplantation, using methods known in the art, as, for example, the methods described in K. R. Stone et al., Porcine and bovine cartilage transplants in cynomolgus monkey: I. A model for chronic xenograft rejection, 63 Transplantation 640–645 (1997).

Where the soft tissue is explanted, the soft tissue xenografts are aseptically harvested, using anesthetic procedure, surgical exposure of joints, removal of the implants and closure of the soft tissue (where the animals are allowed to recover). At the time of the xenograft removal, joint fluid, if present in amounts sufficient to aspirate, is collected from the stifle joints for possible immunologic testing if the gross and histopathologic evaluation of the transplants indicate good performance of the transplanted soft tissue.

The animals which have had meniscus cartilage or articular cartilage xenograft implantations are allowed to recover and are monitored closely until the incisions have healed and the gait is normal. The xenograft samples are collected, processed, and examined microscopically.

Portions of the meniscus cartilage, articular cartilage, heart valve and ligament implants and surrounding tissues are frozen in embedding mediums for frozen tissue specimens in embedding molds for immunohistochemistry evaluation according to the methods known in the prior art. "TISSUE-TEK®" O.C.T. compound which includes about 10% w/w polyvinyl alcohol, about 4% w/w polyethylene glycol, and about 86% w/w nonreactive ingredients, and is manufactured by Sakura FinTek, Torrence, Calif., is a non-limiting example of a possible embedding medium for use with the present invention. Other embedding mediums known to those of ordinary skill in the art may also be used. The remaining implant and surrounding tissue is collected in 10% neutral buffered fomialin for histopathologic examination.

EXAMPLE 3

Assessment Of Primate Response To Implanted Meniscus Cartilage, Articular

Cartilage, Ligament And Heart Valve Soft Tissue Xenografts Treated With α-Galactosidase, Fucosyl and Fucosyltransferase In this example, porcine meniscus cartilage, articular cartilage, ligament and peritoneum heart valve soft tissue implants are treated with α-galactosidase to eliminate α-gal epitopes, as described in Example 2. The soft tissue implants are further treated with fucosyl and fucosyl transferase to cap remaining carbohydrate chains with fucosyl. Fucosyltransferase facilitates the transfer of fucosyl to the xenograft. The fucosyl links to and thus caps the remaining carbohydrate chains. Capping with fucosyl interferes with the ability of the subject's immune system to recognize the xenograft as foreign. The soft tissue implants are transplanted into cynomolgus monkeys, and the primate response to the soft tissue implants is assessed.

Meniscus cartilage and articular cartilage implants from porcine stifle joints, heart valve implants from porcine peritoneum and ligament implants from porcine stifle joints are prepared as the implants are prepared in Example 2 including the α-galactosidase treatment. Prior to implantation into the monkeys, however, the implants are further treated with a predetermined amount of fucosyl and fucosyltransferase, at specified concentrations for a predetermined time and at a predetermined temperature, to cap remaining carbohydrate chains with fucosyl. For example, the implants are immersed in buffer solutions at predetermined concentrations of fucosyl and fucosyl transferase. The implants are incubated for a predetermined time period at a predetermined temperature.

Other molecules, such as N-acetyl glucosarnine in combination with the corresponding glycosyltransferase, can also be used for capping the carbohydrate chains of the implants.

Subsequently, the implants are washed to remove the enzyme and implanted into the monkeys, and the occurrence of an immune response against the xenograft is assessed as described above in Example 2.

EXAMPLE 4

Assessment Of Primate Response To Implanted Meniscus Cartilage. Articular Cartilage, Ligament And Heart Valve Soft Tissue Xenografts Subjected To Freeze Thaw Cycling And Treatment With Proteoglycan-Depleting Factors.

In this example, porcine meniscus cartilage, articular cartilage, ligament and peritoneum heart valve soft tissue implants are prepared and frozen to disrupt, that is, to kill the specimens' cells, as described above in Example 2. The soft tissue implants are further treated with proteoglycan-depleting factors to eliminate substantially the proteoglycans from the xenograft. Subsequently, the xenografts are treated with glycosidase to remove substantially remaining α-gal epitopes from the xenograft, as described in Example 2. Substantial elimination of the proteoglycans and the remaining α-gal epitopes interferes with the ability of the recipient subject's immune system to recognize the xenograft as foreign. The soft tissue implants are transplanted into cynomologous monkeys, and the primate response to the soft tissue implants is assessed.

Meniscus cartilage, articular cartilage and ligament implants from porcine stifle joints and heart valve implants from porcine peritoneum are prepared following the preparation procedures outlined in Example 2 including the sterilization, and freeze/thaw cycling treatments. A chondroitinase ABC solution is then prepared by combining 0.05M Tris-HCL (7.88 gm/liter-MW=157.60), 5mM benzamidine-HCL (0.783gm/liter-MW=156.61), 0.010 M N-ethylmaleimide (1.2513 gm/liter-MW=125.13), and 0.001M phenylmethylsulfonyl fluoride (0.17420 gm/liter-MW=174.2), dissolved in methanol. A mixture of 15 M NaCl (8.775 gm/liter-MW=58.5), penicillin and streptomycin (1% (v/v) 1Oml/liter) along with enzyme in the amount of 1 unit chondroitinase ABC (Sigma #C-3509) Enzyme Solution per 1 ml of solution is added to bring the solution to 1 liter.

Each soft tissue xenograft specimen is incubated in the chondroitinase ABC enzyme solution at a concentration of 1 ml of solution per a 3 mm diameter soft tissue plug. The incubations are performed at a pH of 8.0 and 37 degrees C. in a shaker water bath for 48 hours. After the incubation, each soft tissue specimen is washed in appropriate buffer and the washings are added to the chondroitinase ABC solution. Each soft tissue specimen is then re-incubated with the chondroitinase ABC solution at a concentration of 1 unit chondroitinase ABC (Sigma #C-3509) Enzyme Solution per 1 ml of solution for another 48 hours as described above. Each soft tissue specimen is again washed in appropriate buffer solution, and the washings are added to the chondroitinase ABC solution.

Each soft tissue specimen is then incubated in 1 ml of trypsin solution (1 mg/ml trypsin, 0.15 M NaCl, 0.05 M Na Phosphate) at a pH of 7.2 for 24 hours. The incubation is performed in a shaker water bath at 37 degrees C. Each soft tissue specimen is washed in appropriate buffer solution, and the washings are added to the trypsin solution.

Each specimen is then placed in 1 ml of hyaluronidase solution (0.01 mg/mil testicular hyaluronidase, 0.005 M Benzamidine HCL, 001 M PMSF, 0.010M Nethylmaleimide, 0.005 M Benzamidine HCL, 1% v/v penicillin and streptomycin) at a pH 6.0 for 24 hours. The incubation is performed in a shaker water bath at 37 degrees C. Each soft tissue specimen is then rinsed again in an appropriate buffer solution, and the washings are added to the hyaluronidase solution.

Subsequently, the implants are treated with glycosidase as described above in Example 2, implanted into the monkeys, and the occurrence of an immune response against each of the xenografts is assessed as described above in Example 2.

EXAMPLE 5

Figure 13:
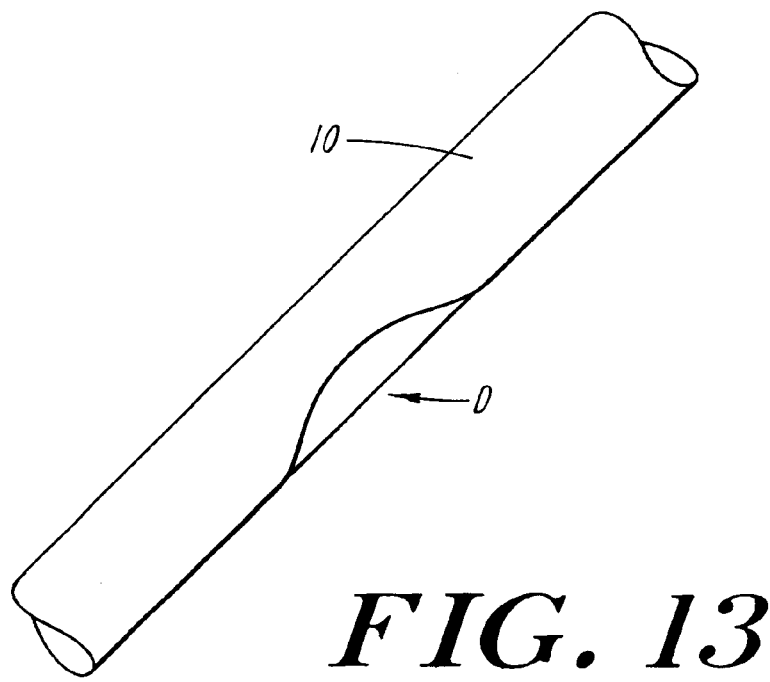
FIG. 13 shows a portion of a bone having a defect.

Assessment Of Response In Mice To Implanted Bone Xenografts Treated With α-Galactosidase And Demineralized Bone Matrix Gel Containing Osteoinductive Factor In this example, porcine bone implants are treated with α-galactosidase to eliminate α-galactosyl epitopes and impregnated with demineralized bone matrix gel containing osteoinductive factor to stimulate the conversion of soft tissue formers in the target defect to osseous tissue formers. The implants are transplanted into mice and the response to the implants is assessed. An exemplary bone portion 10 with a defect D is shown in FIG. 13.

Porcine bone implants are sterilely prepared and surrounding attached soft tissues surgically removed. The bone specimens are washed for at least five minutes with an alcohol, such as ethanol or isopropanol, to remove synovial fluid and lipid soluble contaminants.

The bone specimens are frozen at a temperature ranging from about −35° C. to about −90° C., and preferably at a temperature up to about −70° C., to disrupt, that, is to kill, the specimens' bone cells.

Each bone specimen is cut into two portions. The first bone portion is immersed in a buffer solution containing α-galactosidase at a predetermined concentration. The first bone portion is allowed to incubate in the buffer solution for a predetermined time period at a predetermined temperature. The second bone portion is incubated under similar conditions as the first bone portion in a buffer solution in the absence of α-galactosidase and serves as the control.

At the end of the incubation, the bone portions are washed under conditions which allow the enzyme to diffuse out. Assays are performed to confirm the complete removal of the α-gal epitopes.

The α-galactosidase first bone portions disclosed above are then impregnated with demineralized bone matrix gel containing osteoinductive factor prepared according to methods known in the prior art, such as, for example, John E. Feighan, et al., Induction of Bone by a Demineralized Bone Matrix Gel: A Study in a Rat Femoral Defect Model, 13 Journal of Orthopaedic Research 881–889 (1995).

Figure 14:
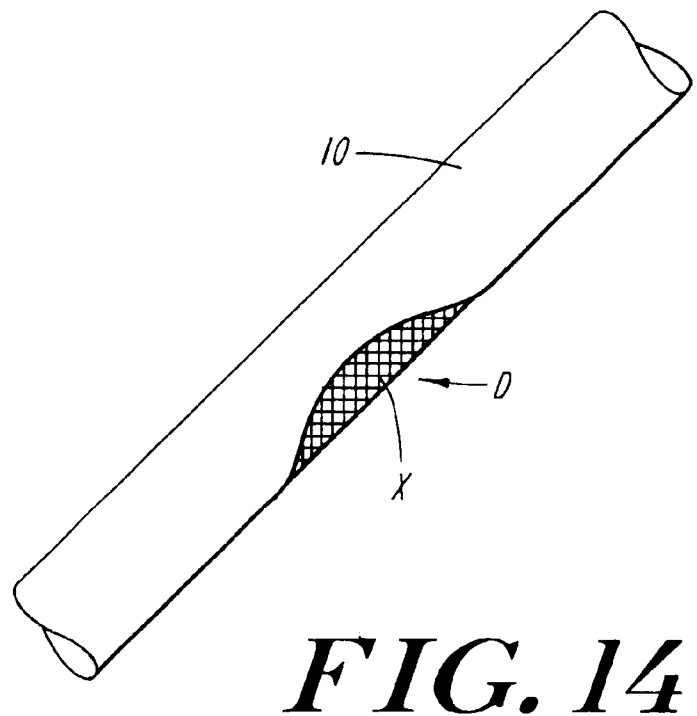
FIG. 14 shows the bone portion of FIG. 13 with a xenograft of the invention in the defect.

The bone samples are implanted in subcutaneous tissues of mice under general inhalation anesthesia following known surgical procedures. Bone is implanted in subcutaneous tissues to evaluate the osteoinductive properties of bone. Any bone formed is evidence of osteoinductive properties. Osteoconductive properties of bone xenograft are evaluated after the xenograft is implanted using bone defective models such as the long bone drill hole model. The implantation procedure is performed under sterile surgical technique, and the wounds are closed with 3-0 vicryl or a suitable equivalent known to those of ordinary skill in the art. FIG. 14 shows the bone portion 10 with the xenograft X (shown crosshatched) in place at the defect D. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-bone xenograft antibodies (i.e., antibodies binding to antigens other than the α-gal epitopes) in serum samples from the transplanted mice. Blood samples are drawn from the transplanted mice on the day of implant surgery and at periodic (e.g., two week) intervals post-transplantation. The blood samples are centrifuged and the serum samples are frozen and evaluated for the anti-Gal and other non-anti-Gal anti-bone xenograft antibody activity.

Anti-Gal activity is determined in the serum samples in ELISA with α-gal-BSA as solid phase antigen, according to methods known in the prior art, such as, for example, the methods described in Galili et al., Porcine and bovine cartilage transplants in cynomolgus monkey. II. Changes in anti-Gal response during chronic rejection, 63 Transplantation 645–651 (1997).

Assays are conducted to determine whether α-galactosidase treated xenografts induce the formation of anti-bone xenograft antibodies. For measuring anti-bone xenograft antibody activity, an ELISA assay is performed according to methods known in the prior art, such as, for example, the methods described in K. R. Stone et al., Porcine and bovine cartilage transplants in cynomolgus monkey: I. A model for chronic xenograft rejection, 63 Transplantation 640–645 (1997).

The bone xenografts are optionally explanted at one to two months post-transplantation, sectioned and stained for histological evaluation of inflammatory infiltrates. Post-transplantation changes in anti-Gal and other anti-bone xenograft antibody activities are correlated with the inflammatory histologic characteristics (i.e., granulocytes or mononuclear cell infiltrates) within the explanted bone, one to two months post-transplantation, using methods known in the art, as, for example, the methods described in K. R. Stone et al., Porcine and bovine cartilage transplants in cynomolgus monkey: I. A model for chronic xenograft rejection, 63 Transplantation 640–645 (1997).

Where the bone xenograft is explanted, the bone xenograft is aseptically harvested, using anesthetic procedure, removal of the implant and closure of the soft tissue. Tissue is harvested for possible immunologic testing if the gross and histopathologic evaluation of the transplants indicate good performance of the transplanted bone. The xenograft samples are collected, processed, and examined microscopically. A portion of the implant and surrounding tissue is frozen in an embedding medium for frozen tissue specimens in embedding molds for immunohistochemistry evaluation according to the methods known in the prior art. "TISSUE-TEKT" O.C.T. compound which includes 10.24% w/w polyvinyl alcohol, 4.26% w/w polyethylene glycol, and 86.60% w/w nonreactive ingredients, and is manufactured by Sakura FinTek, Torrence, Calif., is a non-limiting example of a possible embedding medium for use with the present invention. Other embedding mediums known to those of ordinary skill in the art may also be used. The remaining implant and surrounding tissue is collected in 10% neutral buffered formalin for histopathologic examination.

EXAMPLE 6

Assessment Of Primate Response To Implanted Bone Xenografts Treated With α-Galactosidase and Demineralized Bone Matrix Gel Containing Osteoinductive Factor In this example, porcine bone implants are treated with α-galactosidase and demineralized bone matrix gel containing osteoinductive factor, the implants are transplanted into cynomolgus monkeys, and the primate response to the bone implants is assessed, as described in Example 5. After the bone xenografts are explanted and tissue is harvested for possible immunologic testing, the animals are allowed to recover and are monitored closely until the incisions have healed and the gait of the animals is normal.

EXAMPLE 7

Assessment Of Response In Mice To Implanted Bone Xenografts Treated With α-Galactosidase, Demineralized Bone Matrix Gel Containing Osteoinductive Factor, Fucosyl and Fucosyltransferase In this example, porcine bone implants are treated with α-galactosidase to eliminate α-gal epitopes, as described in Example 5. The implants are further treated with fucosyl and fucosyl transferase to cap carbohydrate chains with fucosyl. Fucosyltransferase facilitates the transfer of fucosyl to the xenograft. The fucosyl links to and thus caps the carbohydrate chains. Capping with fucosyl interferes with the ability of the subject's immune system to recognize the xenograft as foreign. The implants are transplanted into mice, and the response to the bone implants is assessed.

Porcine bone implants are prepared as described in Example 1 including the α-galactosidase treatment. Prior to implantation into the mice, however, the implants are further treated with a predetermined amount of fucosyl and fucosyltransferase, at specified concentrations for a predetermined time and at a predetermined temperature, to cap carbohydrate chains with fucosyl. For example, the samples are immersed in a buffer solution at predetermined concentrations of fucosyl and fucosyl transferase. The samples are incubated for a predetermined time period at a predetermined temperature.

Other molecules, such as n-acetyl glucosamine in combination with the corresponding glycosyltransferase, can also be used for capping the carbohydrate chains of the implants.

Subsequently, the samples are washed to remove the enzyme and implanted into the mice, and the occurrence of an immune response against the xenograft is assessed as described above in Example 5.

EXAMPLE 8
Assessment Of Primate Response To Implanted Bone Xenografts Treated With α-Galactosidase, Demineralized Bone Matrix Gel Containing Osteoinductive Factor; Fucosyl and Fucosyltransferase In this example, porcine bone implants are treated with α-galactosidase, demineralized bone matrix gel containing osteoinductive factor, fucosyl and fucosyltransferase; the implants are transplanted into cynomolgus monkeys and the primate response to the bone implants is assessed, as described above in Examples 5, 6 and 7.

EXAMPLE 9
Assessment Of Response In Mice To Implanted Bone Xenografts Treated With Alcohol and Freeze/Thaw Cycling In this example, porcine bone implants are treated with alcohol and freeze/thaw cycling prior to their transplantation in mice and the response of the mice to the implants is assessed.

Porcine bone implants are sterilely prepared and surrounding attached soft tissues surgically removed. The resultant xenograft is washed in about ten volumes of sterile cold water to remove residual blood proteins and water soluble materials. The xenograft is then immersed in alcohol at room temperature for about five minutes, to sterilize the bone and to remove non-collagenous materials.

After the alcohol washing, the xenograft is treated by again placing the xenograft in an alcohol solution of 70% isopropanol at room temperature for at least five minutes.

Following the alcohol treatment step, the bone implants are placed in a freezer until the xenograft is completely frozen, i.e., no interior warm spots remain which contain unfrozen tissue. Each bone implant is then thawed by immersion in an isotonic saline bath at room temperature (about 25° C.) for about ten minutes.

It should be understood that the bone implants alternatively can be subjected to the above-described freeze/thaw cycling treatment prior to the alcohol treatment step.

The implants are then implanted in the mice and the occurrence of an immune responses against the xenograft is assessed as described above in Example 5.

EXAMPLE 10
Assessment Of Primate Response To Implanted Bone Xenografts Treated With Alcohol and Freeze/Thaw Cycling In this example, porcine bone implants are treated with alcohol and freeze/thaw cycling prior to their transplantation in cynomolgus monkeys and the primate response to the implants is assessed as described above in Examples 5–10.

EXAMPLE 11
Assessment Of Response In Primates To Implanted Soft Tissue And Bone Xenografts Treated With α-Galactosidase And Glutaraldehyde In this example, porcine meniscal, articular cartilage, ligament, peritoneum heart valve and bone implants are treated with alcohol and freeze/thaw cycling, as described above in examples 1–10. They are further treated with between 0.01–0.10% glutaraldehyde, subsequently treated with α-galactosidase, and the primate response to the implants, is assessed as described above in examples 1–10.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing a xenograft formed of a soft or bone tissue for implantation into a human, which comprises
    a. removing at least a portion of the soft or bone tissue from a non-human animal to provide a xenograft;
    b. washing the xenograft in water and alcohol;
    c. subjecting the xenograft to a cellular disruption treatment;
    d. exposing the xenograft to an aldehyde in an amount ranging from about 0.01% to about 0.10%; and
    e. digesting the xenograft with a glycosidase to remove substantially a plurality of first surface carbohydrate moieties from the xenograft whereby the xenograft is substantially non-immunogenic and has substantially the same mechanical properties as the native soft or bone tissue.

2. A method according to claim 1, wherein the step of exposing the xenograft to an aldehyde comprises exposing the aldehyde to an aldehyde selected from the group consisting of glutaraldehyde, formaldehyde, and adipic dialdehyde.

3. A method according to claim 1 further comprising the step of
    after step c, piercing the xenograft.

4. A method according to claim 1 further comprising the step of
    after step c, treating the xenograft with a second enzyme.

5. A method according to claim 4, wherein the second enzyme is selected from the group consisting of ficin and trypsin.

6. A method according to claim 1 further comprising the step of
    after step c, treating the xenograft with one or more agents selected from the group consisting of anticalcification agents, antithrombotic agents, antibiotics, and growth factors.

7. A method according to claim 1 further comprising the step of after step c, sterilizing the xenograft.

8. A method according to claim 7, wherein the sterilizing step comprises sterilizing the xenograft with one or more agents selected from the group consisting of ethylene oxide and propylene oxide.

9. A method according to claim 1 further comprising the step of:

after step c, treating the xenograft with polyethylene glycol.

10. A method according to claim 1 further comprising the step of after step c, exposing the xenograft to one or more agents selected from the group consisting of aliphatic diamine compounds and aromatic diamine compounds.

11. A method according to claim 1, wherein the cellular disruption treatment comprises freeze/thaw cycling.

12. A method according to claim 1, wherein the cellular disruption treatment comprises exposure to gamma radiation.

13. A method according to claim 1, wherein the glycosidase is a galactosidase.

14. A method according to claim 13, wherein the galactosidase is an α-galactosidase.

15. A method according to claim 1 further comprising the step of after step e, treating a plurality of second surface carbohydrate moieties on the xenograft with a plurality of capping molecules to cap at least a portion of the second surface carbohydrate moieties.

16. A method according to claim 15, wherein at least a portion of the capping molecules are a plurality of fucosyl molecules.

17. A method according to claim 15, wherein at least a portion of the capping molecules are a plurality of n-acetyl glucosamine molecules.

18. A method according to claim 1 further comprising the step of after step d, removing substantially a plurality of proteoglycans from the xenograft, wherein the xenograft is a soft tissue.

19. A method according to claim 18, wherein the removing step comprises digesting the xenograft with one or more proteoglycan-depleting factors selected from the group consisting of chondroitinase ABC, hyaluronidase, chondroitin AC II lyase, keratanase, trypsin and fibronectin fragments.

20. A method according to claim 1, wherein the removing step comprises removing the portion of a medial or lateral meniscus having a superior principal surface and an inferior principal surface, each of the principal surfaces having an outer portion being joined by an outer lateral surface, and each of the principal surfaces having an inner portion being joined by an inner lateral surface.

21. A method according to claim 1, wherein the removing step comprises removing the portion of a ligament.

22. A method according to claim 21, wherein the removing step comprises removing with the portion a first block of bone attached to a first end of the portion.

23. A method according to claim 22, wherein the removing step comprises removing with the portion a second block of bone affixed to a second end of the portion opposite the first end.

24. A method according to claim 1, wherein the removing step comprises removing the portion of an articular cartilage.

25. A method according to claim 24, wherein the removing step comprises removing with the portion a layer of subchondral bone.

26. An article of manufacture comprising a substantially non-immunogenic aldehyde-treated, glycosidase-treated xenograft formed of a soft or bone tissue for implantation into a human, produced by the process of a. removing at least a portion of the soft tissue, hard tissue or heart valve from a non-human animal to provide a xenograft;

b. washing the xenograft in water and alcohol;

c. subjecting the xenograft to a cellular disruption treatment;

d. exposing the xenograft to an aldehyde in an amount ranging from about 0.01% to about 0.10%; and e. digesting the xenograft with a glycosidase to remove substantially a plurality of first surface carbohydrate moieties from the xenograft whereby the xenograft is substantially non-immunogenic and has substantially the same mechanical properties as the native soft or bone tissue.

27. An article of manufacture according to claim 26, wherein the aldehyde is selected from the group consisting of glutaraldehyde, formaldehyde, and adipic dialdehyde.

28. An article of manufacture according to claim 26, wherein the xenograft has a plurality of punctures for increasing permeability to agents and enzymes.

29. An article of manufacture according to claim 26 further comprising one or more agents selected from the group consisting of anticalcification agents, antithrombotic agents, antibiotics, and growth factors.

30. An article of manufacture according to claim 26, wherein the xenograft is sterilized.

31. An article of manufacture according to claim 26, wherein the xenograft is a polyethylene glycol-treated xenograft.

32. An article of manufacture according to claim 26, further comprising an agent selected from the group consisting of aliphatic diamine compounds and aromatic diamine compounds.

33. An article of manufacture according to claim 26, wherein the glycosidase-treated xenograft is a galactosidase-treated xenograft.

34. An article of manufacture according to claim 33, wherein the galactosidase-treated xenograft is an α-galactosidase-treated xenograft.

35. An article of manufacture according to claim 26 further comprising a plurality of capping molecules capped on a plurality of second surface carbohydrate moieties on the xenograft.

36. An article of manufacture according to claim 35, wherein the capping molecules comprise a plurality of fucosyl molecules.

37. An article of manufacture according to claim 35, wherein the capping molecules comprise a plurality of n-acetyl glucosamine molecules.

38. An article of manufacture according to claim 26, wherein the xenograft is a thawed, frozen xenograft.

39. An article of manufacture according to claim 26, wherein the xenograft is a gamma-irradiated xenograft.

40. An article of manufacture according to claim 26, wherein the xenograft is a proteoglycan-depleting factor-treated xenograft, and wherein one or more of the proteoglycan-depleting factors is selected from the group consisting of chondroitinase ABC, hyaluronidase, chondroitin AC II lyase, keratanase, trypsin, and fibronectin fragments.

41. An article of manufacture according to claim 26, wherein the portion is of a medial or lateral meniscus having a superior principal surface and an inferior principal surface, each of the principal surfaces having an outer portion being joined by an outer lateral surface, and each of the principal surfaces having an inner portion being joined by an inner lateral surface.

42. An article of manufacture according to claim 26, wherein the portion is of a ligament.

43. An article of manufacture according to claim 42, wherein the portion of the ligament comprises a first block of bone attached to a first end of the portion.

44. An article of manufacture according to claim 43, wherein the portion of the ligament comprises a second block of bone affixed to a second end of the portion opposite the first end.

45. An article of manufacture according to claim 26, wherein the portion is of an articular cartilage.

46. An article of manufacture according to claim 45, wherein the portion of the articular cartilage comprises a layer of subchondral bone.

47. A xenograft formed of a soft or bone tissue for implantation into a human, comprising:

a portion of the soft or bone tissue from a nonhuman animal, wherein the portion includes a plurality of extracellular components, a plurality of substantially only dead cells, and a plurality of proteins within said extracellular components, said protein s crosslinked with an aldehyde in an amount ranging from about 0.01% to about 0.10%, the extracellular components and the dead cells having substantially no surface carbohydrate moieties which are susceptible to glycosidase digestion, and whereby the portion is substantially non-immunogenic and has substantially the same mechanical properties as a corresponding portion of the native soft or bone tissue.

48. A xenograft according to claim 47, wherein the aldehyde is in an amount ranging from about 0.01% to about 0.05% crosslinking the proteins.

49. A xenograft according to claim 47, wherein the portion has capping molecules linked to at least a portion of a plurality of surface carbohydrate moieties on the xenograft, and whereby the xenograft is substantially non-immunogenic.

50. A xenograft according to claim 49, wherein at least a portion of the capping molecules are a plurality of fucosyl molecules.

51. A xenograft according to claim 49, wherein at least a portion of the capping molecules are a plurality of n-acetyl glucosamine molecules.

52. A xenograft according to claim 47, wherein the portion is of a medial or lateral meniscus having a superior principal surface and an inferior principal surface, each of the principal surfaces having an outer portion being joined by an outer lateral surface, and each of the principal surfaces having an inner portion being joined by an inner lateral surface.

53. A xenograft according to claim 47, wherein the portion is of a ligament.

54. A xenograft according to claim 53, wherein the portion of the ligament comprises a first block of bone attached to a first end of the portion.

55. A xenograft according to claim 54, wherein the portion of the ligament comprises a second block of bone affixed to a second end of the portion opposite the first end.

56. A xenograft according to claim 47, wherein the portion is of an articular cartilage.

57. A xenograft according to claim 56, wherein the portion of the articular cartilage comprises a layer of subchondral bone.

58. A method according to claim 1, wherein the step of exposing the xenograft to an aldehyde comprises exposing the xenograft to the aldehyde in an amount ranging from about 0.01% to about 0.05%.

59. An article of manufacture according to claim 26, wherein the xenograft is produced by exposing the xenograft to the aldehyde in an amount ranging from about 0.01% to about 0.05%.

* * * * *